US005773017A

United States Patent [19]

Korunic et al.

[11] Patent Number: 5,773,017
[45] Date of Patent: Jun. 30, 1998

[54] DIATOMACEOUS EARTH INSECTICIDAL COMPOSITION

[75] Inventors: Zlatko Korunic; Paul Fields, both of Winnipeg, Canada

[73] Assignees: Hedley Pacific Ventures Ltd.; Her Majesty the Queen in right of Canada, as represented by the Minister of Agriculture, both of Canada

[21] Appl. No.: 644,490

[22] Filed: May 10, 1996

[30] Foreign Application Priority Data

May 11, 1995 [CA] Canada .................................. 2149164

[51] Int. Cl.⁶ .................................................... A01N 25/12
[52] U.S. Cl. ........................ 424/409; 424/405; 424/406; 424/421; 424/724; 514/63
[58] Field of Search ..................... 424/405, 406, 424/421, 76.9, 409, 724; 524/448, 449, 451; 544/63

[56] References Cited

U.S. PATENT DOCUMENTS

| 596,761 | 1/1898 | Palthorpe | 424/421 |
|---|---|---|---|
| 1,861,127 | 5/1932 | McLane | 424/421 |
| 2,941,923 | 6/1960 | Albert | 424/421 |
| 3,028,305 | 4/1962 | Alvin et al. | 424/421 |
| 3,159,536 | 12/1964 | Marotta | 424/406 |
| 3,235,451 | 2/1966 | Odeneal | 424/421 |
| 3,917,814 | 11/1975 | Hedges et al. | 424/406 |
| 4,927,635 | 5/1990 | Loschiavo | 424/409 |
| 5,186,935 | 2/1993 | Tucker | 424/410 |
| 5,264,213 | 11/1993 | Shibahara et al. | 424/409 |
| 5,576,007 | 11/1996 | Ikeda et al. | 424/408 |

FOREIGN PATENT DOCUMENTS

| 86197 | 9/1976 | Australia . |
|---|---|---|
| 582200 | 3/1989 | Australia . |
| 594539 | 3/1990 | Australia . |
| 0 337 212 A3 | 10/1989 | European Pat. Off. . |
| 0 579 834 A1 | 1/1994 | European Pat. Off. . |
| 6-80510 | 3/1994 | Japan . |
| 86/02807 | 5/1986 | WIPO . |
| 94/09626 | 5/1994 | WIPO . |

OTHER PUBLICATIONS

Ebeling, W. (1971) Sorptive dusts for pest control. Ann. Rev. Entomol. vol. 16: 123–158.
Quarles, Q. (1922.a) Diatomaceous earth for pest control. The IPM Practitioner. vol. 14: 1–11.
Quarles, Q. (1922.b) Silica gel for pest control. The IPM Practitioner. vol. 14: 1–11.
Wright, C.G., and H.E. Dupree (1984) Evaluation of German cockroach mortality and several insecticidal dust formulations. J. Georgia Entomol. Soc. vol. 19: 216–223.
Celite, "Material Safety Data Sheet", No. 2200, Rev. No. 1, May 28, 1993.
Degussa Corporation, "Material Safety Data Sheet", MSDS #1756, Jan. 25, 1995.
Dryacide Australia Ltd., "Material Safety Data Sheet", Sep.25, 1990.

*Primary Examiner*—Neil S. Levy
*Attorney, Agent, or Firm*—Morgan Lewis Bockius LLP

[57] ABSTRACT

An insecticidal dust composition comprising an effective amount of diatomaceous earth (DE) in combination with an effective amount of silica selected from the group consisting of precipitated silica and aerogel silica, the DE and silica mixed in different proportions by weight depending on the type of DE, and may preferably be about 95% to 65% DE to about 5% to 35% silica.

10 Claims, 14 Drawing Sheets

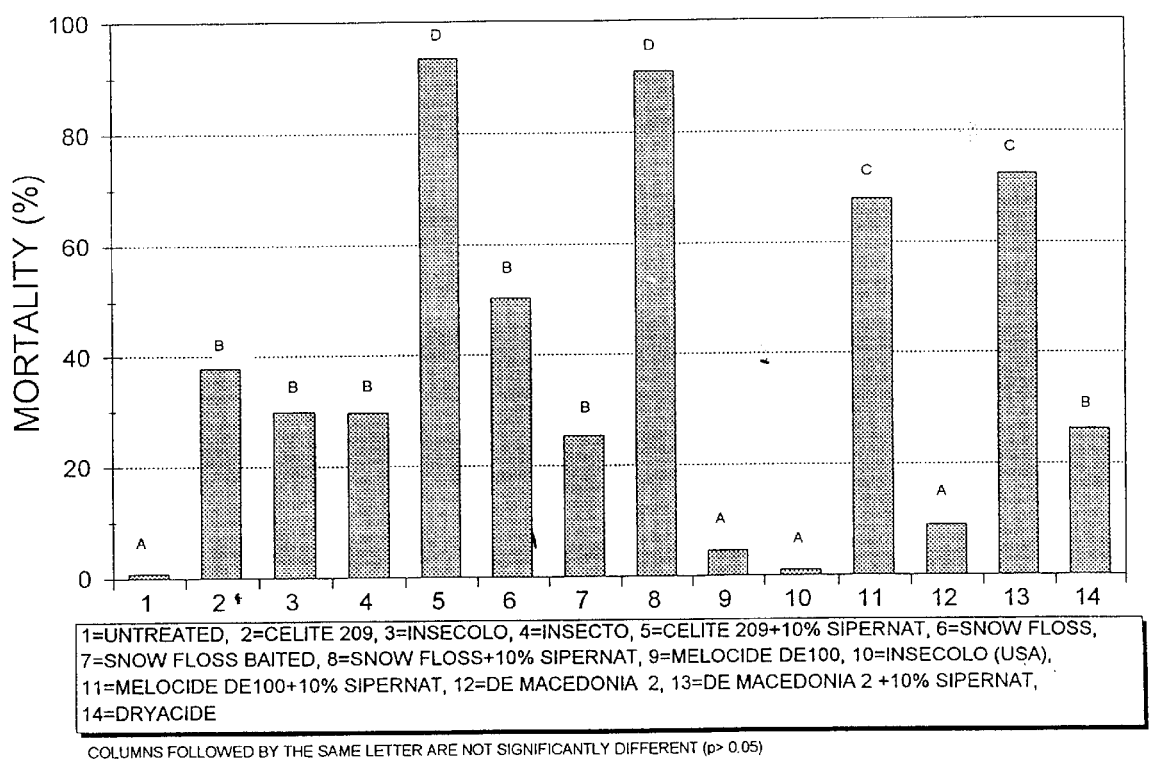

Fig 1. MORTALITY OF RUSTY GRAIN BEETLE EXPOSED (1 DAY) TO VARIOUS DIATOMACEOUS EARTH (300 PPM)

1=UNTREATED, 2=CELITE 209, 3=INSECOLO, 4=INSECTO, 5=CELITE 209+10% SIPERNAT, 6=SNOW FLOSS, 7=SNOW FLOSS BAITED, 8=SNOW FLOSS+10% SIPERNAT, 9=MELOCIDE DE100, 10=INSECOLO (USA), 11=MELOCIDE DE100+10% SIPERNAT, 12=DE MACEDONIA 2, 13=DE MACEDONIA 2 +10% SIPERNAT, 14=DRYACIDE

COLUMNS FOLLOWED BY THE SAME LETTER ARE NOT SIGNIFICANTLY DIFFERENT ($p > 0.05$)

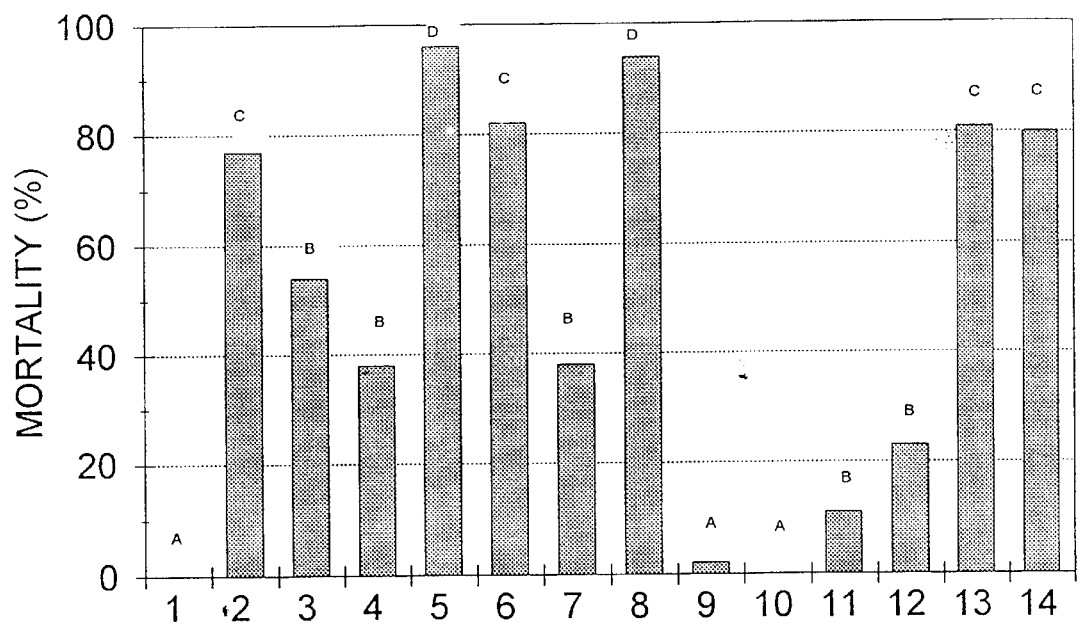

Fig 2. MORTALITY OF RED FLOUR BEETLE EXPOSED (7 DAYS) TO VARIOUS DIATOMACEOUS EARTH (1000 PPM)

1=UNTREATED, 2=CELITE 209, 3=INSECOLO, 4=INSECTO, 5=CELITE 209+10% SIPERNAT, 6=SNOW FLOSS, 7=SNOW FLOSS BAITED, 8=SNOW FLOSS+10% SIPERNAT, 9=MELOCIDE DE100, 10=INSECOLO (USA), 11=MELOCIDE DE100+10% SIPERNAT, 12=DE MACEDONIA 2, 13=DE MACEDONIA 2+10% SIPERNAT, 14=DRYACIDE

COLUMNS WITH THE SAME LETTER ARE NOT SIGNIFICANTLY DIFFERENT ($p > 0.05$)

DIATOMACEOUS EARTH INSECTICIDAL COMPOSITION

FIELD OF THE INVENTION

The present invention relates to an insecticidal composition, and more particularly to an insecticidal powder composition, based on diatomaceous earth, for use in dry environments such as grain stores and food processing facilities.

BACKGROUND OF THE INVENTION

Due to increased public concern relating to the toxicity of insecticide residues in grain and in the environment and the occurrence of insecticide resistant insect strains, there has been a need to search for new approaches for insect pest control.

It has been well known for centuries that stored grain can be protected from insect attack by mixing powders or dust into the grain. Common materials included plant ash, lime, dolomite, certain types of soil and diatomaceous earth. Diatomaceous earth is known to be one of the most effective naturally occurring insecticidal dusts (Ebeling, 1971).

Single-celled plants called diatoms live in seas and lakes and extract silicon from water into their shells producing a hydrated amorphous silica skeleton. When the diatoms die, the tiny shells sink, and in some instants these shells can build up into thick layers. Eventually the shells of these deposits were fossilized and compressed into a soft, chalky rock that is called diatomaceous earth (DE). Today, DE is prepared for commercial use by quarrying, drying and milling. The only change to DE during this process is the reduction of the moisture content and mean particle sizes. The result is a fine, talc-like powder or dust, not toxic to mammals. It is extremely stable and does not produce toxic chemical residues or react with other substances in the environment (Quarles, 1992a).

According to the EPA (Environmental Protection Agency, USA), RED (Registration Eligibility Documents) Facts, 21T-1020, September, 1991, diatomaceous earth, described as amorphous silicon dioxide, has a physical mode of action to control insects. It has low to moderate acute toxicity (Category III) and has not been associated with silicosis. Also, according to the International Agency for Research on Cancer (IARC), amorphous silicon dioxide belongs to group 3—not a carcinogen. Due to its negligible toxicity, in the USA, diatomaceous earth is exempt from the requirement of tolerance of legal residue limits, when applied to growing crops and agricultural commodities after harvest, to animals, or to food as feed processing and storage areas. Amorphous silicon dioxide is "Generally Recognized as Safe" (GRAS) as a food additive (21 CRF 182.90 and 182.1711). Consequently, the EPA concluded that human health risk from diatomaceous earth is low and unmeasurable. Also, there is no evidence to suggest that use of this material as a pesticide in accordance with approved labelling, presents a hazard to non-target organisms, other than arthropods.

Besides controlling stored-product insects, DE is very useful for pest management in the home and garden field. It controls many different insects (Quarles, 1992a).

Stored Product Protection

The first commercial formulations of DE became widely available in the 1950's. Between 1965 and 1970 a series of studies on DE were conducted by USDA in USA (Quarles 1992a), in former Czechoslovakia and former Yugoslavia (Croatia). After these initial studies, experiments were also run in other countries, such as Australia and Egypt. In several experiments, DE provided better protection from insects than malathion, particularly over the long term. At that time, relatively large amounts of DE were added to grain to provide protection, e.g. 3500 ppm, (3.5 kg/tonne). Between the 1980's and 1990's, the problem of using relatively large amounts of DE has been reduced through the use of improved DE formulations that contain baits and attractants (for example, Insecto*, Insecolo*, Insectigone*), or very low percentage of silica gel coated on DE particles and 1% flouride (Dryacide*) (Table 1). But, the concentrations of current formulations of DE registered use for the protection of stored grain are still too high (500 ppm to 3600 ppm) to be accepted by the grain industry.

There are some other formulations of DE mixed with different substances such as rotenone or pyrethrins (usually 0.1 to 0.2%). Boric acid, bendiocarb, diazinon and chlorpyrifos were also tested in some experiments (Wright and Dupress, 1984; Belford, 1990).

There are several problems associated with DE treatment of grain that limit its widespread use and acceptance. These dusts at their current rates decrease the bulk density of grain (test weight) (Table 2 and 3), reduce the flowability of grain, leave visible residues (chalky-white appearance) and thereby reduce the grade because it is classed as containing foreign material. Diatomaceous earth has been thought to cause excess wear on machinery, and workers complain because of airborne dust during treatment and movement of grain. Some of these problems could be solved or reduced if the products were used at lower rates, but the rates of current registered formulations of DE are too low to control insects.

It is thus an object of the present invention to increase the efficacy of DE so that insects are controlled, but the mentioned disadvantages are minimized.

SUMMARY OF THE INVENTION

In accordance with the present invention there is provided an insecticidal dust composition comprising an effective amount of DE in combination with an effective amount of silica selected from the group consisting of precipitated silica and silica aerogel. The DE and silica are mixed in different proportions by weight depending on the type of DE, and may preferably be about 95% to 65% DE to about 5% to 35% silica aerogel.

Mixed with DE, the silica increases the active surface area, increases the flowability of DE and prevents the clumping or caking of DE particles, giving a better particle size distribution.

In a preferred embodiment of the present invention, the DE is about 90% by weight of a marine DE, such as Celite 209 diatomaceous earth or its equivalent. The silica is preferably about 10% by weight of a precipitated amorphous silica, such as Sipernat 50S or its equivalent A preferred marine DE is sold under the Celite 209 trade name and is available from Celite Corp., Quincy, Wash. A preferred silica is precipitated amorphous silica sold under the Sipernat 50S trade name which is available from Degussa Canada, Ltd., Burlington, Ontario.

It has been determined that the efficacy of compositions mixed in accordance with the present invention against insects is significantly higher than the efficacy of current commercial formulations of DE. More particularly, by using such compositions, the concentration needed to control insects can be greatly reduced. As well, because of the use of lower concentrations of such formulations, some of the problems previously associated with insecticidal uses of DE in grains are greatly reduced:

- visible residues on grain are greatly reduced; at very low concentrations of 50 to 100 ppm, there are no visible residues;
- there is less airborne dust during the treatment and manipulation of the grain;
- the influence of dust on the flowability of grain and problems with machinery are reduced;
- tolerant species against DEs can be controlled much easier and even under higher moisture content (M.C.) of the grain (14%).

It has been determined that compositions mixed in accordance with the present invention have only a slightly reduced tapped density compared with current commercial DE formulations (Table 4). The main disadvantage of silica aerogel, low tapped densities which make them dusty to work with and bulky to transport and store, are not evident in the mixed formulations of DE and silica aerogel.

BRIEF DESCRIPTION OF THE DRAWINGS

These and other advantages of the invention will become apparent upon reading the following detailed description and upon referring to the drawings in which:

FIG. 1 is a graph reflecting testing results of the application of certain DE compositions to control rusty grain beetles.

FIG. 2 is a graph reflecting testing results of the application of certain DE compositions to control red flour beetles.

Figure 3A:
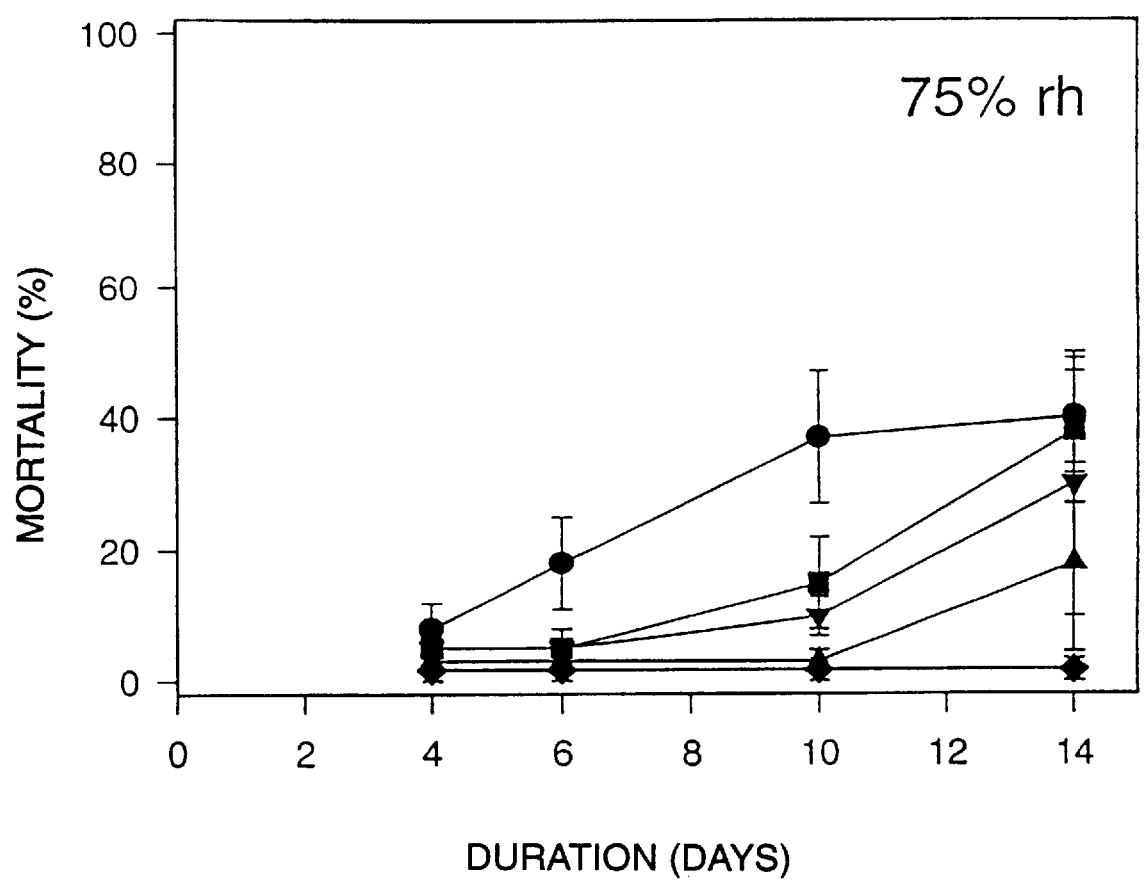
FIGS. 3A and 3B are graphs reflecting the control of the rice weevil in containers treated with 2 DE formulations.

While the invention will be described in conjunction with an example embodiment(s), it will be understood that it is not intended to limit the invention to such embodiment (s). On the contrary, it is intended to cover all alternatives, modifications and equivalents as may be included within the spirit and scope of the invention as defined by the appended claims.

DETAILED DESCRIPTION OF THE INVENTION

The components for the composition mixture according to the present invention are different natural formulations of DE and precipitated amorphous silicon dioxide. A preferred composition according to the present invention is a mixture of DE Celite 209 and silicon dioxide Sipernat 50S. A preferred marine DE is sold under the Celite 209 trade name and is available from Celite Corp., Quincy, Wash. A preferred silica is precipitated amorphous silica sold under the Sipernat 50S trade name by Degussa Canada, Ltd., Burlington, Ontario.

Mixing of these two components is done in the weight ratio 90% Celite 209 and 10% Sipernat 50S. The resultant dust composition should be dry with a declared moisture content: Celite 209 with a maximum 6% moisture content and Sipernat 50S with a maximum 6% moisture content.

EXAMPLE I

Celite 209 and Sipernat SOS, in a weight ratio of 9:1, were mixed together at room temperature for at least 10 minutes. When mixing is done properly, Sipernat 50S (white in colour) cannot be seen in the mixture. The mixture looks like Celite 209 (buff colour), and has a specific gravity of about 33.7 $Kg/m^3$ and physical and chemical properties are almost identical to those of Celite 209. The only significant difference is in the content of amorphous silicon dioxide which is present in the mixture at about 88% (in Celite 209, amorphous silicon dioxide is present at about 86.7% by weight). Some differences in particle size distribution between the mixture and Celite 209 exist. Celite 209 has a median particle size of from 7 to 8.2 microns with 75.3% particles under 16 microns or 49.1% under 8 microns. The mixture of Celite 209 and Sipernat 50S (synergized Celite 209) has a median particle size of 6.3 microns with 81.2% of the particles being under 16 microns or 57.3% under 8 microns.

Celite 209 was mixed with Sipernat 50S at different weight ratios: 50:50; 60:40; 70:30; 80:20; 90:10 and 95:5. The most acceptable results were obtained with the mixture of 90% by weight of Celite 209 and 10% Sipernat 50S (synergized Celite 209). The efficacy of this mixture against insects is significantly higher than the efficacy of current known commercial formulations of diatomaceous earth (Tables 5 to 9, FIGS. 1,2) (Table 1, FIGS. 1,2).

Field Tests 1994

Grain treated with 50 ppm of synergized Celite 209 reduced insect populations after one month, but by the second month there was a resurgence in insect populations (Table 10, 11, 12). Mites, which included both predacious and grain-feeding species, were reduced by over 98% at 50 ppm. After one month, 300 ppm had eliminated the rusty grain beetle and mites and had reduced the red flour beetle populations by 88 to 99% compared to the untreated grain.

The bulk density of the wheat was slightly reduced, 2.1 kg/hl or 2.7% by the application of 50 ppm of synergized Celite 209. At 300 ppm, the bulk density or test weight was reduced by 4.6 kg/hl or 6% (Table 13). Neither of the dosages caused a reduction in grade because the grain was down graded due to other factors. Treatment of grain with 50 ppm did not cause any noticeable reduction in flowability or any increase in dust in the air. At 300 ppm there was a noticeable reduction in grain flow and an increase in dust in the air.

Structural Treatments

Figure 3B:
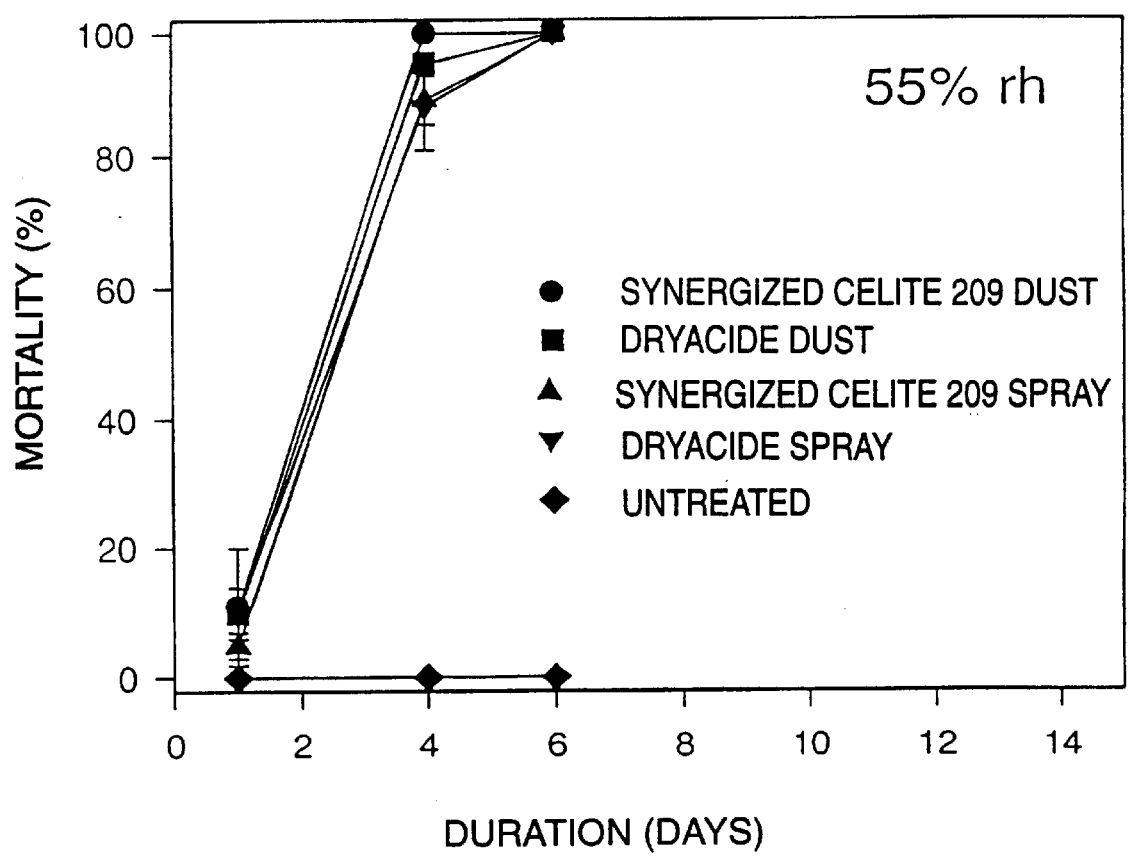
Figure 4A:
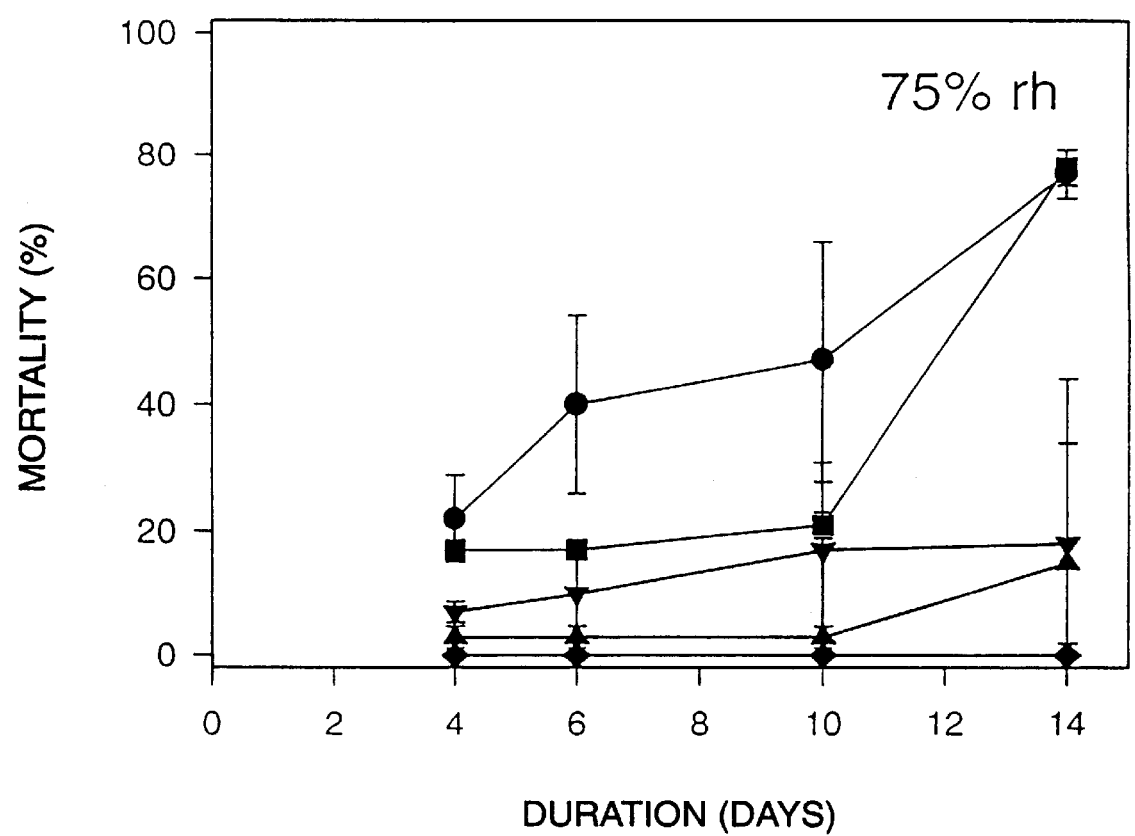
FIGS. 4A and 4B are graphs reflecting the control of the red flour beetle in containers treated with 2 DE formulations.
Figure 4B:
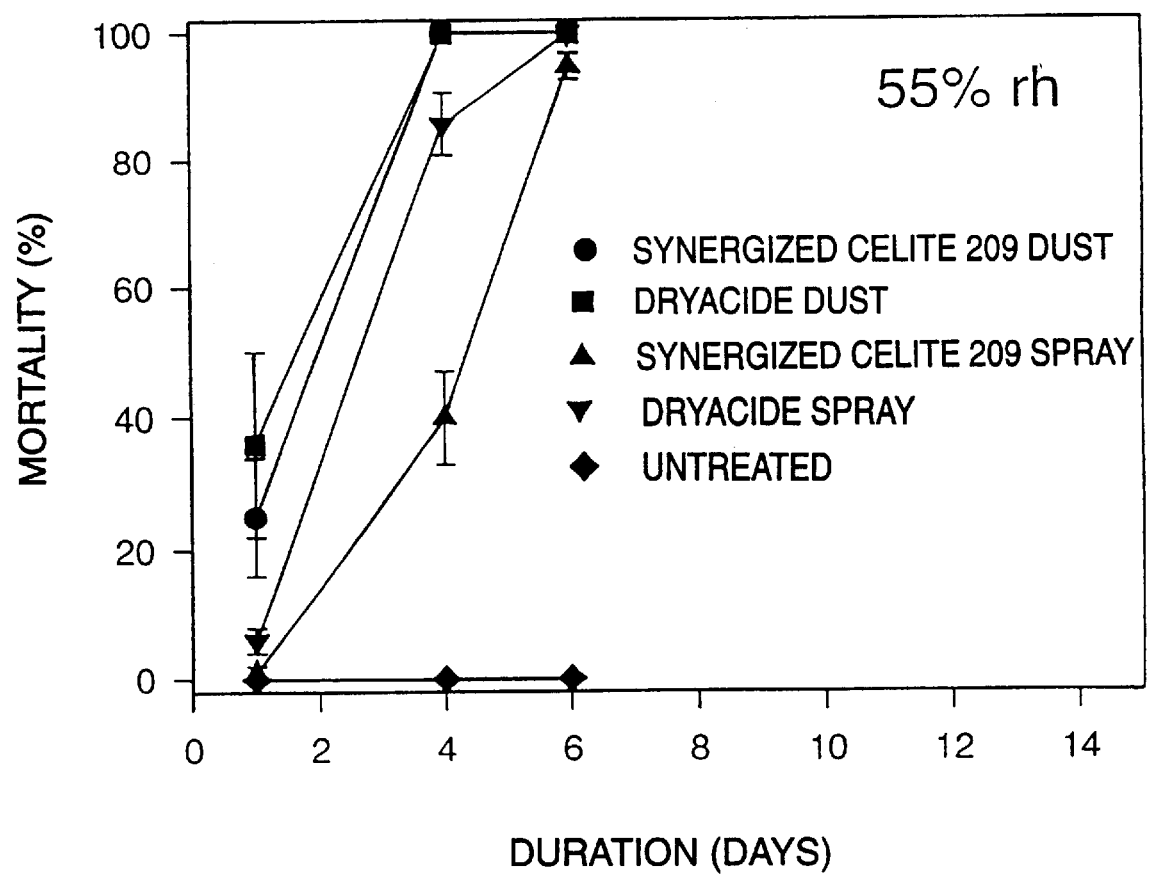
Figure 5A:
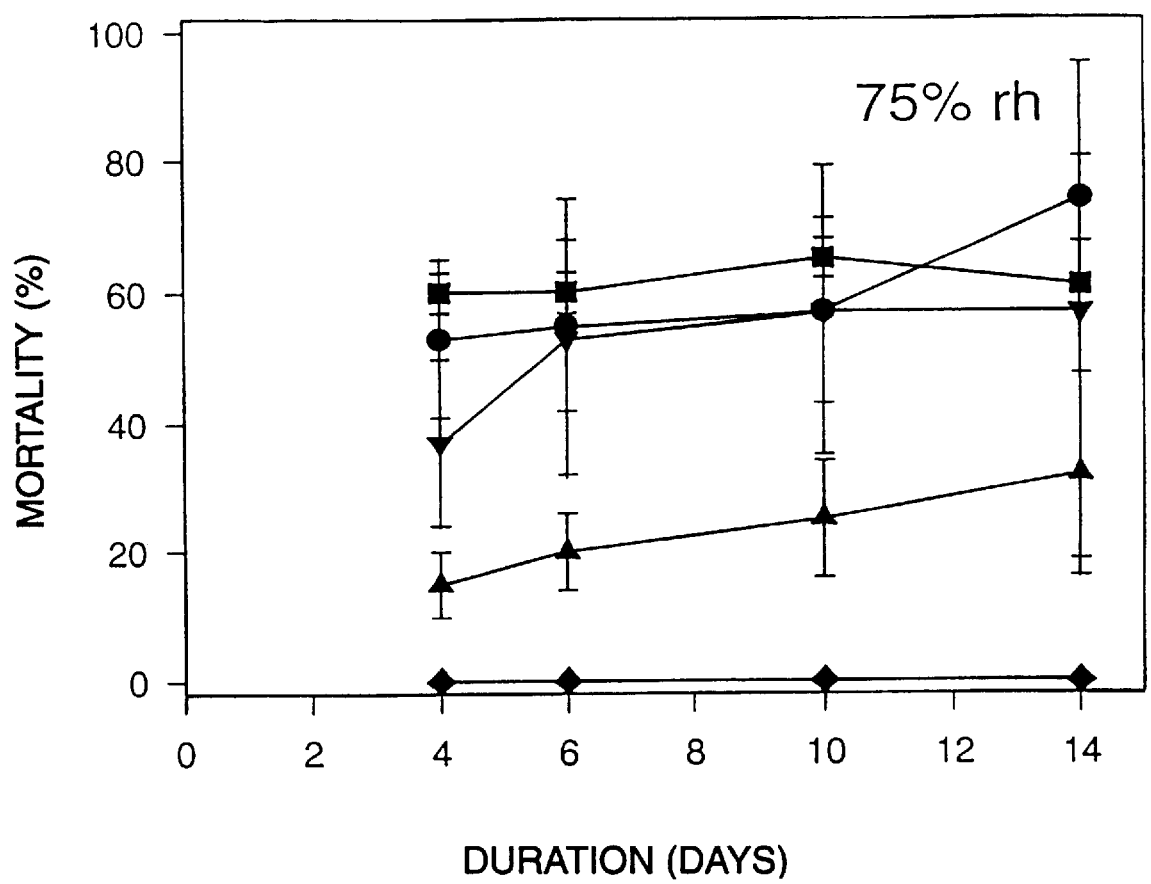
FIGS. 5A and 5B are graphs reflecting the control of the lesser grain borer in containers treated with 2 DE formulations.
Figure 5B:
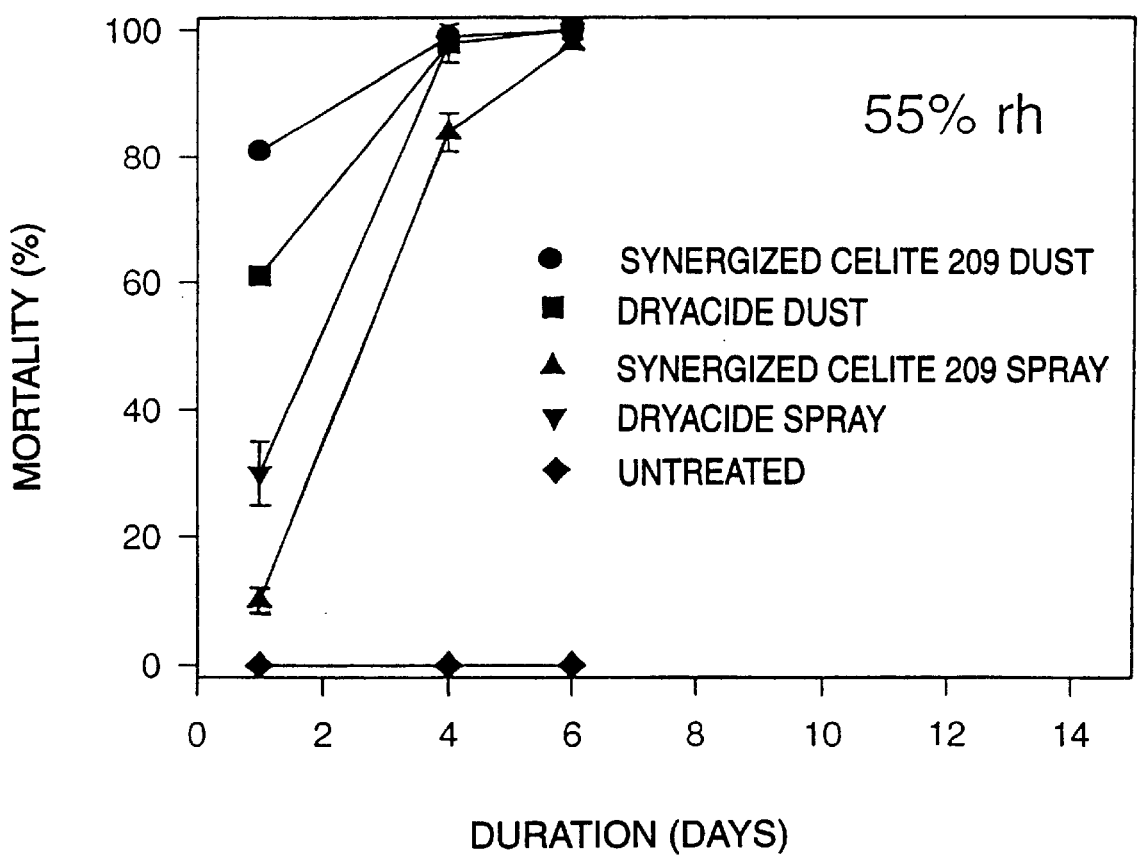

FIGS. 3A and 3B depict the mortality (X±SEM) of rice weevil in containers treated with DE. FIGS. 4A and 4B depict the mortality (X±SEM) of red flour beetle in containers treated with DE. FIGS. 5A and 5B depict the mortality (X±SEM) of lesser grain borer in containers treated with DE.

There was good control of insects after one week at 55% rh. At 75% rh, dry application killed about 50% of the population, whereas spray application was ineffective. In all treatments the rusty grain beetle was controlled within 2 days. The dry application of the dust (Dust, FIGS. 3A, 3B, 4A, 4B, 5A and 5B) was always more effective than the wet slurry application (Spray, FIGS. 3A, 3B, 4A, 4B, 5A and 5B). Syngerized Celite 209 had similar efficacy as Dryacide, a commercial diatomaceous earth used extensively in Australia to treat empty grain storage structures.

EXAMPLE II

Due to results obtained with synergized Celite 209, other DEs collected from different deposits from around the world were mixed with Sipernat 50S at different ratios. The tapped density of the mixture was measured to discover the influence of the synergist (Sipernat 50S) on tapped density of DE (Table 4). Tapped density (DIN ISO 787/11) is the ratio of mass to volume of a substance which has been compacted in accordance with set conditions, expressed in g/l. The acceptable lower limit was taken as about 265 g/l for tapped density of formulations of DE can be the values for currently registered and accepted light formulations of DE as an insecticide, range from 285 to 292 g/l (Table 4). From the results reflected in Table 4, DEs from different deposits can be mixed with synergist Sipernat 50S up to 30% (w/w). For Example DE Macedonia can be mixed with synergist in the ratio up to 70:30; DE Japan 2—70:30; Celite 209 only 90:10; Snow Floss* cannot be mixed with synergist (too light and dusty); DE Japan 3 cannot be mixed with synergist; Melocide* DE 100, extremely dense fresh water DE—70:30; Melocide Super Fine—70:30; DE Mexico 2—70:30; DE Mexico 1—80:20; DE San Diego—80:20; DE Japan 1—80:20.

By mixing these synergized formulations, insecticidal results were much better in comparison with the results obtained using such DEs without the synergist (Tables 14 to 19, FIGS. 1, 2). The synergistic action of DE Celite 209 and Sipernat 50S is clearly shown in Table 9.

By using the synergized formulation of different DEs and especially of synergized Celite 209, the concentration needed to control insects can be greatly reduced; (Table 19). Using these much lower concentrations, the efficacy of synergized Celite 209 and other tested synergized formulations of DE is significantly higher in comparison with unsynergized formulations of DE (FIGS. 1 and 2, Tables 5 to 9, 14 to 19). These concentrations are 1.7 to 70 times lower than what is recommended for current registered DE.

According to the results of measurement of tapped densities and the bioassay results presented in the Figures and Tables herein, especially Tables 4, 18 and 19, it is concluded that the efficacy of almost every DE against insects, even with low activity, can be increased by mixing with precipitated amorphous silicon dioxide, of which Sipernat 50S is an example, or with similar formulations of precipitated silica or aerogel silica in different ratios. The ratio depends on the tapped density of DE itself and the efficacy of DE and the mixture. Due to the results presented in Tables 4, 18 and 19, for tested DEs, the preferred mixing ratio (w/w) of DE to amorphous silicon dioxide (Sipernat 50S or the like) is as follows:

|  | DE | Amorphous Silica |
| --- | --- | --- |
| Celite 209 | 90 | 10 |
| DE Macedonia | 80 | 20 |
| DE Mexico 2 | 80 | 20 |
| DE Mexico 1 | 80 | 20 |
| De San Diego | 80 | 20 |
| DE Japan 1 | 80 | 20 (estimated - no sample) |
| DE Japan 2 | 70 | 30 (probably, no sample) |
| Melocide DE 100 | 70 | 30 |
| Melocide Super Fine | 70 | 30 |

The same principle of mixing can be applied to different diatomaceous earths and different formulations of precipitated and aerogel silicas (Wessalon*, Dri-Die SG-68*, etc.). Prior to making decisions about the needs for mixing and the ratio of mixing, some data about DE must be analyzed, particularly the biological activity of DE itself against insects, the tapped density, pH of DE the influence of synergist on the changing of tapped density, type of DE (marine or fresh water DE). It is desirable to have the data about the particle size distribution and to know something about the shape of diatoms in the formulation. By analyzing these data, it is possible to predict the efficacy of synergized formulations and to determine the ratio of mixing.

With respect to these other DEs used in these further experiments, the following is a general product description.

DE Macedonia has the median particle size of 9.7 microns and 73.5% of particles under 16 microns and the tapped density of 551 g/l; mixed with Sipernat 50S in the ration 70:30 the median particle size is 5.3 microns, 100% of particles are under 16 microns and tapped density is 310 g/l. Snow Floss has the median particle size of 6.3 microns, 75.3% of particles under 16 microns and the tapped density 261 g/l. Melocide DE has the median particle size of 11.1 microns, 65.6% of particles are under 16 microns and the tapped density is 726 g/l. Mixed with Sipernat 50S tapped densities are: 468 g/l (ratio 9:10), 379 g/l (ratio 80:20), 324 g/l (ratio 70:30) and 220 g/l (ratio 60:40).

Melocide Super Fine has the median particle size of 4.54 microns, 100% particles under 16 microns and the tapped density of 600 g/l. Mixed with Sipernat 50S tapped densities are: 436 g/l (ratio 90:10), 324 (ratio 80:20), 266 g/l (ratio 70:30). DE Mexico 1 has the median particle size of 11.8 microns, 67.1 particles are under 16 microns and the tapped density is 375 g/l. Mixed with Sipernat 50S tapped densities are: 299 g/l (ratio 90:10), 265 g/l (ratio 80:20), 213 g/l (ratio 70:30).

Information is not available yet for the median particle size and particle size distribution for DE Mexico 2, DE Japan 1, 2 and 3 and for DE San Diego. Tapped densities and the influence of Sipernat 50S on the tapped density are presented in Table 19.

DE Mexico 1 and Mexico 2 are very similar. The shape of diatoms are almost identical. DE San Diego has the shape of diatoms very similar to Melocide DE 100—rounded diatoms like a tube. Perma Guard belongs to this group of DE. For these diatomaceous earths the prints using the electron microscopy were made in Agriculture and Agri-Food Research Centre, Winnipeg and are available upon request.

METHODS OF TESTING

Laboratory Tests

The insects (rusty grain beetle, *Cryptolestes ferrugineus* (Stephens); lesser grain borer, *Rhyzopertha dominca* (Fabricius); rice weevil, *Sitophilus oryzae* (Linnaeus); and red flour beetle, *Tribolium casataneum* (Herbst) used in the tests were unsexed mixed age adults reared at 30° C. All cultures were started from insects collected from the field in the last 5 years.

The tests were conducted at 30° C. unless stated otherwise. Uninfested, clean, certified Canada Hard Red Spring seed wheat with 5% cracked wheat was mixed with DE at 50 ppm (0.05 kg/t) to 1000 ppm (1 kg/t). Fifteen grams of wheat was placed into vials with 50 rusty grain beetle or 25 adults of the other species. For each condition, there were 5 vials, with only one species/vial. After 1 to 14 days the insects were separated from the wheat by sifting the contents of the vials over a sieve with 200 mm openings, and the number dead and alive noted.

For the surface application tests, plastic boxes, 10 cm wide×10 cm long×4 cm high, were roughened with sandpaper to allow insects to walk normally. There were two types of application methods. For dry application, 0.03 g (3 g/m$^2$) of inert dust (Dryacide or Synergized Celite 209) was placed in the centre of the box and spread evenly across the bottom of the box with a paint brush. For the spray application, 1 ml of water with 0.07 g (7 g/m$^2$) of inert dust (Dryacide or Synergized Celite 209) was sprayed on to the box bottom with an aerosol applicator (Crown, Fisher Scientific Ltd.). The aerosol can was held 30 cm from the box during application and the box was left to dry for 2–3 hours. One gram of cracked wheat was placed in the centre of each box. There were 20 insects/box and three (75% rh) to four (55% rh) replicates for each treatment. Four stored-grain adult insects were used: rusty grain beetle, (*Cryptolestes ferrugineus* (Stephens)); rice weevil (*Sitophilus oryzae* (Linnaeus)); lesser grain borer (*Rhyzopertha dominica* (Fabricius)) and red flour beetle (*Tribolium castaneum* (Herbst)). Mortality was observed at 1 to 14 days. The boxes were held at 25°±1° C. in the dark, and the whole experiment was run either at 55±5% rh or 75±5% rh.

Field Tests 1994

Trials were conducted in 80 tonne capacity galvanized steel farm storage bins. The bins were circular with a diameter of 6 m and a wall height of 6 m. Prior to moving the wheat into the bins, thermocouple wires for measuring temperature were placed into each bin. During July 1994, the wheat was heated to approximately 25° C. and moisturized to approximately 13.5% moisture content (mc). Wheat was treated at 50 or 300 parts per million (ppm) by adding synergized Celite 209 to the wheat at the base of a screw auger that moved the grain from a truck into the bin. The amount of synergized Celite 209 to be applied was determined by the weight of wheat in the truck.

Rusty grain beetles (*Cryptolestes ferrugineus* (Stephens)) were reared in the laboratory in four liter jars at 30° C., 16% mc wheat with 5% cracked wheat and 5% wheat germ. The strain used was collected from farms in southern Manitoba in 1991. Red flour beetles (*Tribolium castaneum* (Herbst)) were reared in four liter jars on wheat flour with 5% brewers yeast at 30° C. and 65% relative humidity (rh) and held at 20° C. several weeks before the release. The strain used was collected from a farm near Landmark, Manitoba in 1991. For the release on Aug. 4, 1994, the entire contents of 11 jars, wheat and rusty grain beetles, were spread onto the grain surface in each of the three bins. To estimate the numbers of insects released, three jars were sifted and the number of adults counted. There were 1443±181 (mean±standard error of the mean) rusty grain beetle adults per jar resulting in approximately 15,000 rusty grain beetles being released into each bin. For the red flour beetle, all insects were sifted off the flour from the culture, placed onto the grain surface and covered with wheat. Two jars were counted, with a mean of 11,180±494 adults. In each bin the insects from six jars were released to give a total of approximately 67,000 red flour beetles/bin. For each species there were larvae and pupae released at the same time, but no estimate of these stages was made. These two insects are the major pest insects in Canadian stored grain, and they represent the range of sensitivity to diatomaceous earth. The rusty grain beetle is very sensitive and the red flour beetle is one of the most tolerant stored-grain pests.

For each bin there was 20 sampling points ten at the top surface and ten 1 meter below the top surface. Efficacy was measured by two different methods. In each bin, 20 probe pit-fall traps were placed in the grain and the trapped insects removed every two weeks. These traps are one of the most sensitive insect detection methods currently available. For the second method, grain samples (approximately 900 g) were taken from 20 points in each bin using deep bin cup grain triers. Insects were extracted using Berlese funnels, the same method used by the Canadian Grain Commission to detect insect infestations.

1995 Field Tests Methods and Materials

Field trials were conducted at three sites in southern Manitoba, Canada. At the Agriculture and Agri-Food Canada Winnipeg Research Centre's Experimental Farm at Glenlea, three 80 tonne capacity galvanized steel farm storage bins (5.6 m diameter and 6.0 m wall height) were used with approximately 16 to 21 tonnes of wheat in each bin. At the University of Manitoba Experimental Farm at Glenlea, four 60 tonne capacity galvanized steel farm storage bins (4.3 m diameter and 3.2 m wall height) were used with approximately 16 tones of wheat in each bin.

Hard Red Spring wheat harvested in August and September 1995 was used in all tests. Wheat was harvested, treated and placed directly into three respective storage bins from Sep. 2 to 6, 1995, for Winnipeg Research Centre, from Aug. 29 to Sep. 1, 1995, for University of Manitoba, and from Aug. 29 to Sep. 7, 1995, for Morden Research Centre. Wheat was treated at 75 or 100 parts per million (ppm) by adding Protect-It (trademark for composition of 90% by weight Celite 209 (trademark) and 10% by weight Sipernat 50S (trademark)) as a dust to the wheat at the base of a screw auger that moved the grain from truck to bin. The amount of Protect-It to be applied was determined by the weight of wheat in the truck. The amount of Protect-It to be applied was measured volumetrically, the method of measurement to be used by farmers and elevator operators, and then weighed to verify the exact amount applied. At University of Manitoba and Morden Research Centre spray application was also used for one lot of wheat. Protect-It was applied as a 15 to 20% slurry (wt:wt) to the wheat as it fell from the truck into the base of the auger. We used an 11.4 L backpack sprayer (Spray Doc, Gilmour Groups, Mississauga, Ontario, L5S 1P7) at 10 psi equipped with a flat nozzle (TeeJet standard flat spray tip, models 11002VS and 110015VS, Spraying Systems Co., Wheaton, Ill. 60189-7900). The auger, 7 inch diameter with a 16 hp motor turning at 3600 rpm, moved wheat at 0.42–0.6 tonnes/minute. This combination gave an application rate of 100ppm.

Prior to unloading, two 2.5 kg samples of untreated wheat were collected from each truck load using a 1 m long profile probe (Dean Gamet Manufacturing Co., Minneapolis, Minn.). This probe collects approximately 700 g of wheat all along the depth of the probe. A profile probe was also used to collect four 1–1.5 kg samples of treated wheat, immediately after the wheat was placed in the bin. Samples were taken 1.5 meters north, west, south and east of the centre of each bin. Profile probe samples taken on successive dates were taken directly at the surface sampling points, and/or directly between adjacent surface sampling points.

Rusty grain beetles were reared in the laboratory in 4 L jars at 30° C., 16% moisture content wheat with 5% cracked wheat and 5% wheat germ. The strain used was collected from farms in southern Manitoba in 1991. Red flour beetles were reared in 4 L jars on wheat flour with 5% brewers yeast at 30° C. and 65% rh. The strain used was collected from a farm near Landmark, Manitoba in 1991. The entire contents of several jars (5 jars Winnipeg Research Centre, 3 jars University of Manitoba and 3 jars Morden Research Centre) of wheat and rusty grain beetles, were spread onto the grain surface of each bin on September 11 at Winnipeg Research Centre, on September 2 at University of Manitoba and on September 12 at Morden Research Centre. Prior to release, beetles were removed from the wheat, pooled, divided into groups weighing 0.49 gm (the estimated mass of 2,000 adult rusty grain beetles), and then returned to the same wheat. To estimate the numbers of insects released, the number of adults in five 0.49 gm groups were counted. There were 1937.8±13.6 (mean+standard error of the mean) rusty grain beetle adults per jar, resulting in approximately 10,000, 6,000 and 6,000 rusty grain beetle adults being released into each bin at Winnipeg Research Centre, University of Manitoba and Morden Research Centre respectively. For the red flour beetle, all insects were sifted off the flour from the culture, placed onto the grain surface and covered with wheat. The insect in 4 jars were counted, with a mean of 15293.5±399.5 adults. The insects from 2, 1 and 1 jars respectively at Winnipeg Research Centre, University of Manitoba and Morden Research Center were released to give a total of approximately 30,000, 15,000 and 15,000 red flour beetles/bin. For each species, there were larvae and pupae released at the same time, but no estimate of these stages was made. These two insects were chosen for the experiments because they are the major pest insects in Canadian stored grain and they also represent the range of sensitivity to diatomaceous earth, with the rusty grain beetle being very sensitive and the red flour beetle being one of the most tolerant stored-grain pests.

For each bin there were 20 sampling points at Winnipeg Research Centre and 10 points at University of Manitoba and Morden Research Centre due the smaller size of the bins. Half of the sampling points were slightly below the grain surface and half 1 meter below the surface. Adjacent to each sampling point, a temperature probe, constructed from thermocouple wire and wooden dowelling, was used to measure the grain temperature at 15 and 85 cm below the surface. Efficacy was measured by four different methods. In the first method, a probe pitfall trap (Storegard WB Probe II, Trécé Incorporated, P.O. Box 6278, Salinas, Calif. 93912) was placed at each sampling point. These traps are larger than the traps used in the previous field trial (White et at. 1990). Traps were placed in the grain on September 14 at Winnipeg Research Centre and University of Manitoba and on September 19 at Morden Research Centre. The trapped insects were removed weekly between September 21 to October 24. After October 24, traps were emptied every two weeks. Probe-pit fall traps are one of the most sensitive insect detection methods currently available.

For the second method, insects were extracted from grain samples to provide a quantitative estimate of field populations. Grain samples were collected at each sampling point using a 225 g capacity grain tier (Dean Gamet Manufacturing Co., Minneapolis, Minn.) on October 5 at Winnipeg Research Centre and University of Manitoba, and on October 3 at Morden Research Centre. All other samples for extraction were collected by profile probe. Insects were extracted by sieving the wheat using a sieve with 2.00 mm openings (Canadian Standard Sieve Series No. 10, Combustion Engineering Inc., St. Catherines, Ontario), and the number live and dead were noted. In addition, live adults and larvae were extracted from 0.5 and 1 kg wheat samples using a berlese funnel placed under a 60 watt lamp for a 12 hour period.

In addition to measuring field populations, mortality was estimated by confining a known number of beetles to cages. In each bin, three 3 L ventilated glass jars, containing 300 adult rusty grain beetles and 300 adult red flour beetles, were filled with grain from the bin immediately after treatment. Each jar was placed in the wheat with the top even with the grain surface. At the end of October, the jars were removed from the bins. Grain was taken from each jar and the insects were extracted using the sieving methods.

Control samples of wheat collected from the truck before treatment, and samples of wheat collected from the bin immediately after treatment and at the end of the experiment, were divided into two groups. The first group was submitted to the Canadian Grain Commission for grading and independent analysis of grain bulk density and percentage dockage. The second group was analyzed at the Winnipeg Agriculture Canada Research Centre for moisture content, grain bulk density and percentage dockage. Wheat moisture content was measured using a dielectric moisture meter (AACC method 44-11) (Model 919, Labtronics, Winnipeg, MB, Canada). Grain bulk density was determined using the Ohaus 0.5 1 measure and Cox funnel. Dockage was removed using a sieve with 2.00 mm openings.

1995 Field Tests Results

Figure 6:
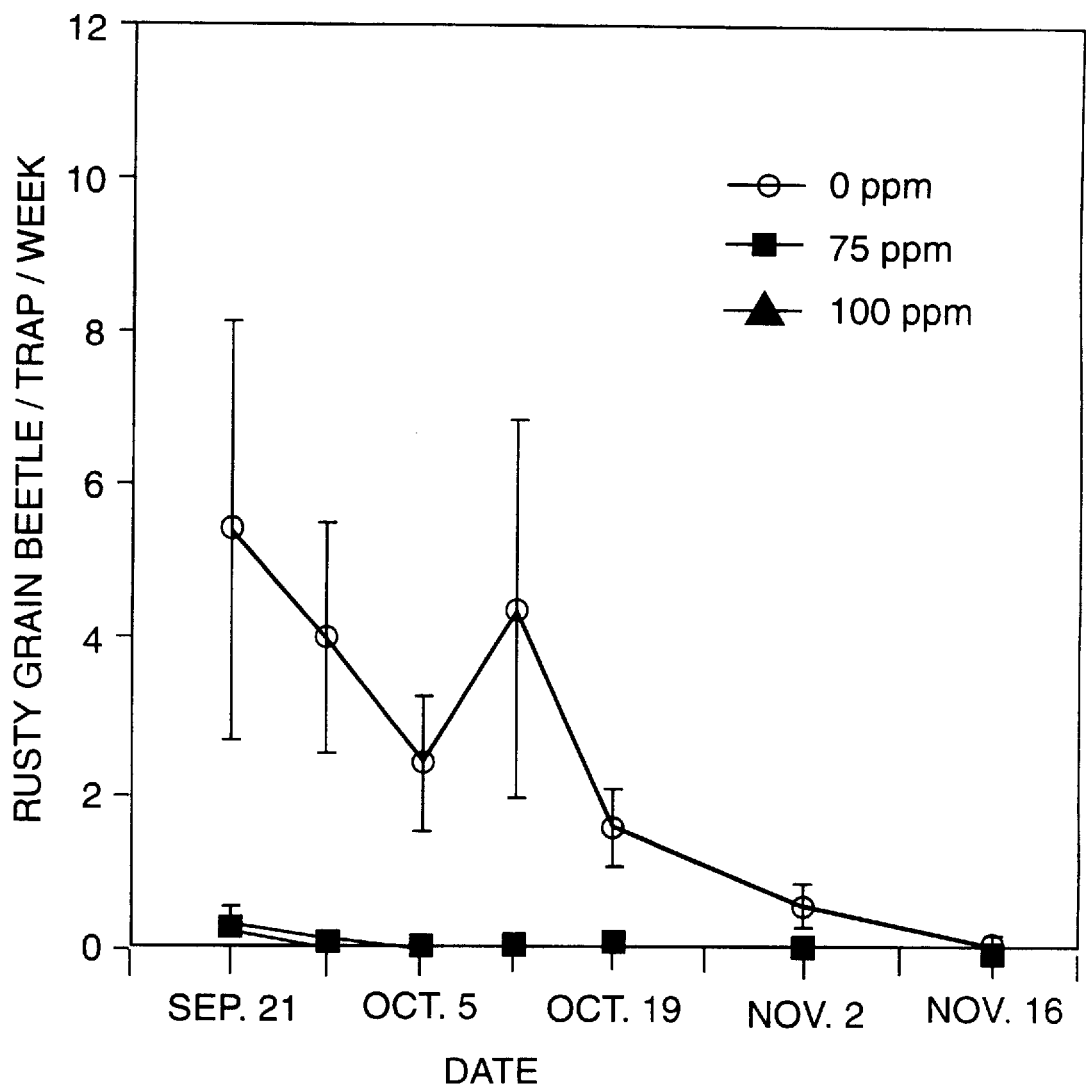
FIGS. 6, 7 and 8 are graphs reflecting the control of rusty grain beetles in wheat treated with different concentrations of Protect-It (trademark for composition of 90% by weight Celite 209 (trademark) and 10% by weight Sipernat 50S (trademark)).
Figure 7:
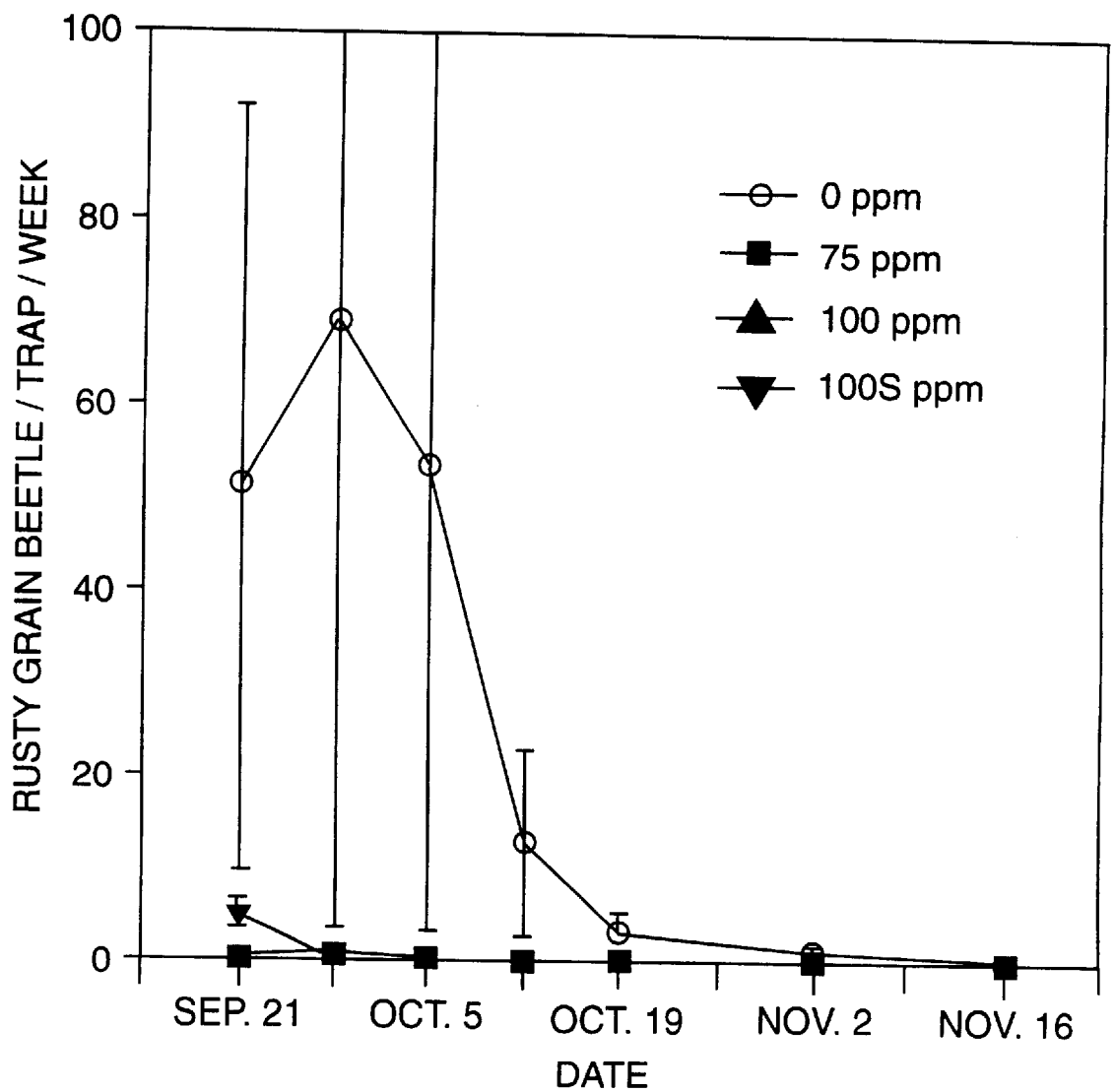
Figure 8:
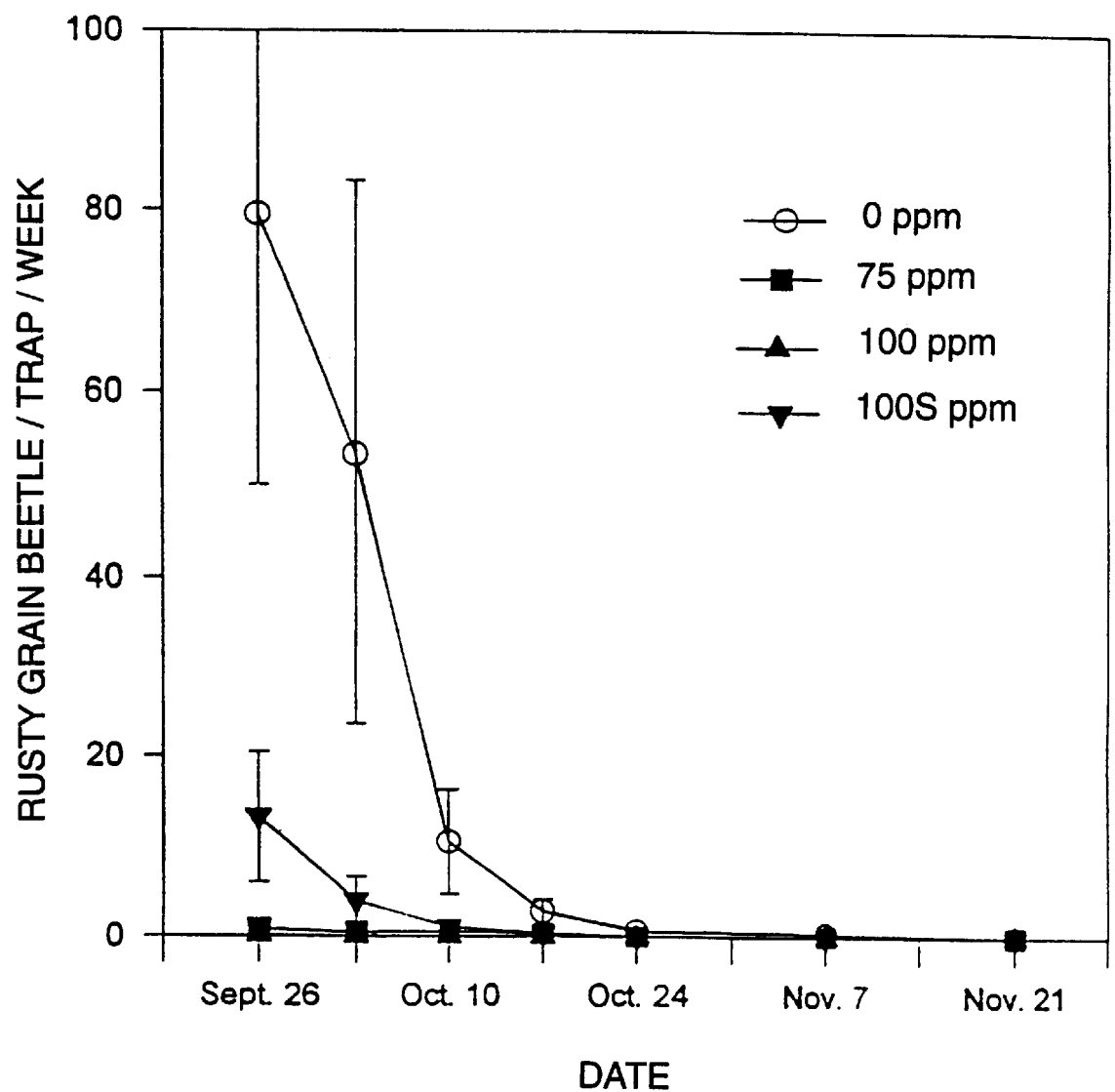
Figure 9:
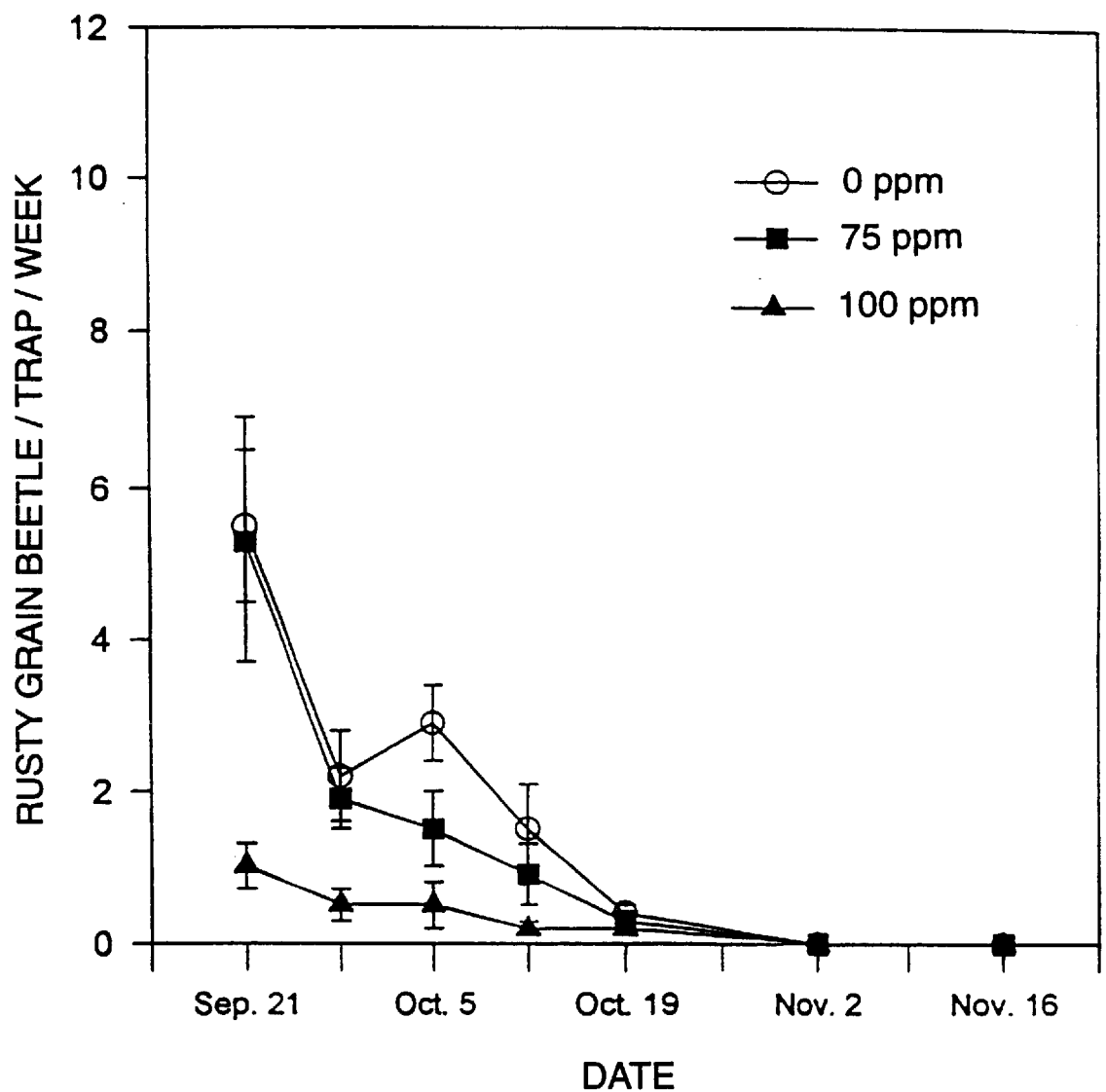
FIGS. 9, 10 and 11 are graphs reflecting the control of the red flour beetle in wheat treated with different concentrations of Protect-It diatomaceous earth at different research centres.
Figure 10:
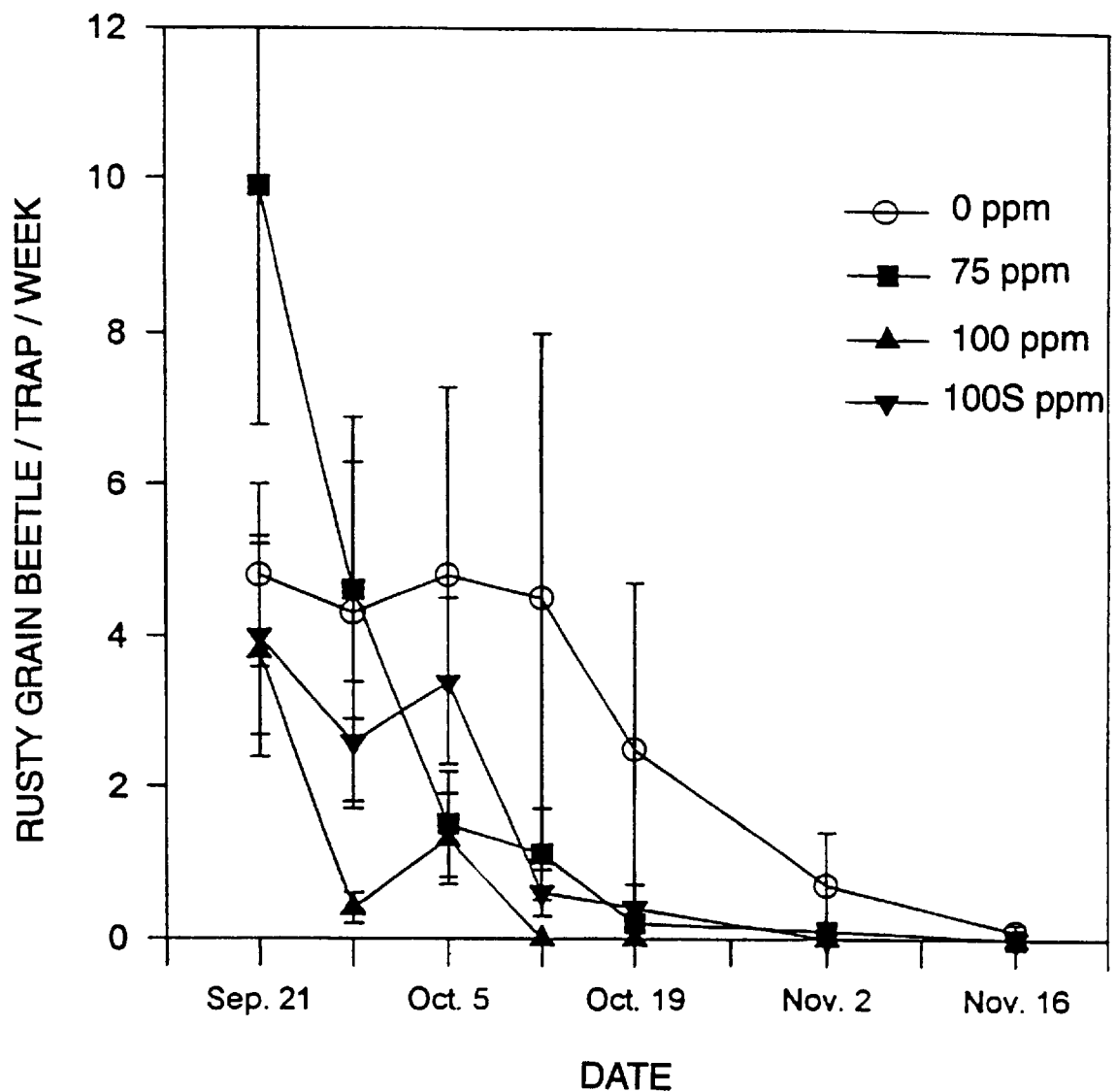
Figure 11:
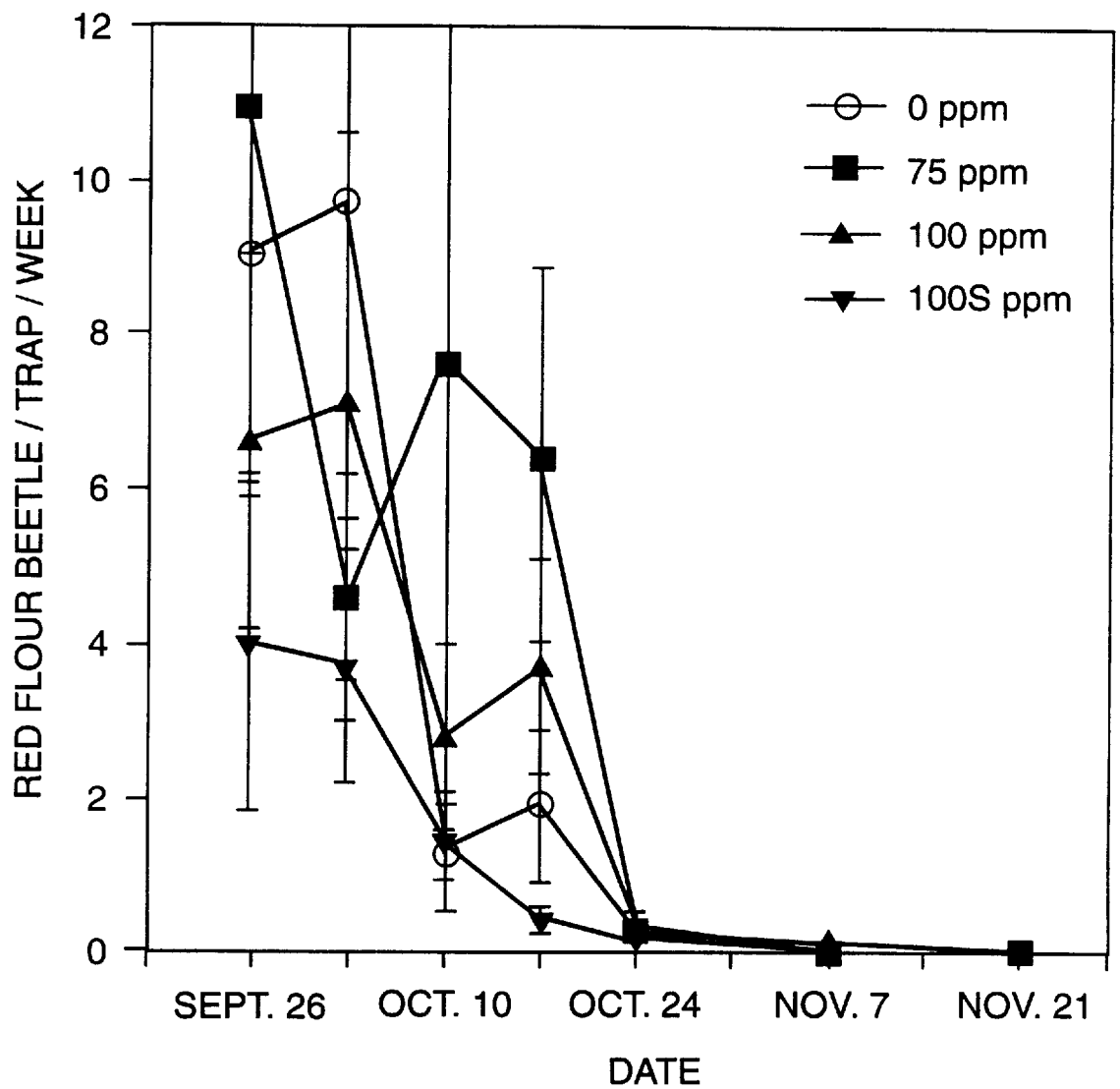

Rusty grain beetle populations, as measured by probe pitfall traps, were significantly lower in bins treated with Protect-It (FIGS. 6 to 8, Table 20). The probe pitfall trap measurements are presented in FIGS. 6 to 8 which depict the number of insects (±SEM) caught in probe pitfall traps from wheat treated with different concentrations of Protect-It diatomaceous earth. For the total number of insects trapped over the 5 week sampling period rusty grain beetle populations were reduced by over 90% by 75 and 100 ppm dust applications, and 87.4 to 99.9% by 100 ppm spray application. The red flour beetle is more resistant to diatomaceous earth than the rusty grain beetle. Only at Winnipeg Research Centre did the 100 ppm application of Protect-It consistently suppress populations (FIGS. 9 to 11, Table 20). The probe pitfall trap measurements presented in FIGS. 9 to 11 depict the number of insects (±SEM) caught in probe pitfall traps from wheat treated with different concentrations of Protect-It diatomaceous earth. At the other sites there were always differences between the populations in treated and untreated bins (100 ppm). For the reduction in the total number of red flour beetles trapped over the 5 weeks, mortality varied from 0–83% (Table 20).

The number of insects extracted from grain samples to provide a quantitative estimate of field population using a profile probe are presented in Table 21. Mortality of the rusty grain beetle at Winnipeg Research Centre was 100% at 75 and 100 ppm, at University of Manitoba 100% at all concentrations and methods of application used, and at Morden 100% at 75 and 100 ppm dusting and at 87.5% spraying. See FIGS. 6, 7 and 8 respectively. Mortality of the red flour beetle at Winnipeg Research Centre was 66.6% (significant difference), at University of Manitoba population was too low in untreated bin to make any conclusion, and at Morden 78.9% at 75 ppm dusting, 84.2 ppm dusting, and 94.7% spraying (significant difference). See FIGS. 9, 10 and 11 respectively.

Mortality of the rusty grain beetle and the red flour beetle in glass jars held in the bins during the field tests, dockage (%, w/w), moisture content, test weight and the temperature of grain in the jars are presented in the Tables 22, 23 and 24). At Winnipeg Research Centre mortality (or significant population reduction) of the rusty grain beetle was over 99% at 75 and 100 ppm dusting, at University of Manitoba 99 and 100% at 75 and 100 ppm, respectively, and 93.4 at 100 ppm spraying, at Morden 98.7 and 100% at 75 and 100 ppm, respectively, and 92.6% at 100 ppm spraying. The mortality of the red flour beetle was at Winnipeg Research Centre 75.6 and 62.5% at 75 and 100 ppm, respectively (not significant), at University of Manitoba 0.7 and 45.3% at 75 and 100 ppm spraying, respectively (not significant), and 88.9% at 100 ppm dusting (significant difference), at Morden 46.8, 47.2, and 26.1% at 75 ppm dusting, 100 ppm dusting and 100 ppm spraying, respectively.

Protect-It at 75 and 100 ppm, due to test weight measurements, did not change the grade of treated Hard Red Spring Wheat measured and graded by Canadian Grain Commission (Table 25).

Protect-It at very low concentrations on wheat, 75 to 100 ppm as a dust and 100 ppm as a spray (the only formulation of DE in the world recommended for grain spraying), under the field conditions controls the rusty grain beetle and greatly suppresses the red flour beetle. At 300 ppm, Protect-It controls the red flour beetle. These concentrations are much lower than the concentrations (500 ppm to 3500 ppm) of other registered formulations of diatomaceous earth in the world.

Thus it is apparent that there has been provided in accordance with the invention a diatomaceous earth insecticidal composition that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

LITERATURE CITED

Belford, W. R. (1990) Insecticidal composition comprising boric acid and silica gel sorbed onto inorganic particles. CA Australian Patent 594,539. 113: 54369x.

Ebeling, W. (1971) Sorptive dusts for pest control. Ann. Rev. Entomol. 16: 123–158.

Quarles, W. (1992.a) Diatomaceous earth for pest control. The IPM Practitioner. 14.: 1–11.

Quarles, W. (1992b) Silica gel for pest control. The IPM Practioner. 14: 1–11.

Wright, C. G., and H. E. Dupree (1984) Evaluation of German cockroach mortality and several insecticidal dust formulations. J. Georgia Entomol. Soc. 19: 216–223.

TABLE 1

REGISTERED FORMULATIONS OF DIATOMACEOUS EARTH

| Formulation | Producer/ Country | Type of DE | Field of Use | Concentration in Stored-Product Field |
|---|---|---|---|---|
| DiaFil | CR Minerals Corp., Golden, CO, USA | fresh water | home & garden as dust, agriculture | 3500 ppm |
| Dryacide | Dryacide Australia Pty. Ltd., Maddington, Western Australia | fresh water | agriculture | 1000 ppm as dust and slurry application |
| Insecolo | Hedley Pacific Ventures, Ltd., Vancouver, Canada | marine | home & garden applied wet and as dust | |
| Insecolo | Hedley Pacific Ventures, Ltd., Vancouver, BC, Canada, Production in USA | fresh water | home & garden as dust | |
| Insectigone | Chemfree Environment Inc., Kirkland, QB, Canada | marine | home & garden as dust | |
| Insecto | Insecto Product Inc., Orange, CA, USA | marine | home & garden agriculture | 500 to 1000 ppm |
| Melocide DE 100 | White Mountain of America, Inc., Eldora, Iowa, USA | fresh water | home & garden, agriculture | 900 to 3500 ppm |
| Melocide DE 200 (granules) | White Mountain of America, Inc., Eldora, Iowa, USA | fresh water | agriculture | 3500 ppm |
| Perma Guard SF Grain Treatment | Perma-Guard Inc., Albuquerque, NM, USA | fresh water | agriculture | 1000 to 2000 ppm |
| Shellshocks | Dorsey, Inc., South Williamsport, PA, USA | fresh water | household pests as dust | |

TABLE 2

THE INFLUENCE OF DIFFERENT FORMULATIONS OF DIATOMACEOUS EARTH ON TEST WEIGHT OF CANADA HARD RED SPRING WHEAT

| Concentrations (ppm) | Test Weight (kg/hl) | | | | | Grade[2] |
|---|---|---|---|---|---|---|
| | Celite 209 | Insecolo | Snow Floss | Melocide DE 100 (dust) | Melocide DE 200 (granules) | |
| 0 | 78.1 | 78.1 | 78.2 | — | | 1 |
| 10 | — | — | 76.9 | — | | 1 |
| 25 | — | — | 75.5 | — | | 1 |
| 50 | — | 75.1 | 74.4 | — | | 1,2 |
| 100 | — | 73.8 | 73.0 | — | | 2 |
| 250 | — | 72.9 | 71.8 (?) | — | | 2,3 (?) |
| 500 | 72[1] | 72.2[1] | 72.1[1] | 72.9[1] | | 2 |
| 1000 | 72.8[1] | 72.0[1] | 72.0[1] | 72.1[1] | 73.8 | 3,2 |
| 3200 | 71.7 | — | — | 71.8[1] | 72.5 | 3,2 |

[1]Would probably be classed as feed grade due to visible residues
[2]Test minimums for Canadian Hard Red Spring: grade 1, 75 kg/hl; grade 2, 72 kg/hl; grade 3, 69 kg/hl.

TABLE 3

THE INFLUENCE OF DIFFERENT FORMULATIONS OF DE ON TEST WEIGHT OF CANADA HARD RED SPRING WHEAT CV. KATEPWA

| | Concentrations (ppm) | | | |
|---|---|---|---|---|
| | 100 | | 600 | |
| Formulation | Test Weight (kg/hl) | Reduction (%) | Test Weight (kg/hl) | Reduction (%) |
| Marine DE | | | | |
| Untreated | 78.2 | 0 | 78.0 | 0 |
| Insecolo (Hedley) | 73.3 | 6.3 | 71.8 | 8.0 |
| Synergized Celite 209 | 72.5 | 7.3 | 71.7 | 8.1 |
| Insecto | 72.9 | 6.8 | 71.8 | 8.0 |
| DE Macedonia | 74.0 | 5.4 | 72.1 | 7.6 |
| DE Japan 3 | 74.1 | 5.2 | 72.3 | 7.3 |
| DE Japan 2 | 74.2 | 5.1 | 72.2 | 7.4 |
| Dryacide | 73.0 | 6.7 | 71.6 | 8.0 |
| Perma Guard | 73.9 | 5.5 | 72.0 | 7.6 |
| Insecolo (USA) | 75.2 | 3.8 | 72.4 | 7.2 |
| DE Mexico | 74.5 | 4.8 | 72.7 | 6.8 |
| DE Japan 1 | 74.0 | 5.4 | 72.0 | 7.6 |

TABLE 4

TAPPED DENSITY[1] OF DIATOMACEOUS EARTHS MIXED WITH PRECIPITATED SILICA SIPERNAT 50S

| Formulation | | Tapped Density* (g/l) Sipernat 50S - Percentage in Mixture | | | | | |
|---|---|---|---|---|---|---|---|
| | | 0 | 10 | 20 | 30 | 40 | 50 |
| Marine Diatomaceous Earths | DE Canada (B.C.) | 593 | — | — | — | — | — |
| | DE Macedonia (Europe) | 551 | 420 | 315 | 310 | 187 | — |
| | De Japan 2 | 469 | 383 | 306 | — | — | — |
| | Insecolo (HPV, Canada) | 292 | — | — | — | — | — |
| | Insectigone (Canada) | 290 | — | — | — | — | — |
| | Celite 209 (USA) | 300 | 265 | 239 | 202 | 162 | 158 |
| | Snow Floss (USA) | 261 | 239 | 218 | 209 | 155 | — |
| | Insecto (USA) | 288 | — | — | — | — | — |
| | DE Japan 3 | 227 | 201 | — | — | — | — |
| Fresh Water Diatomaceous Earths | Melocide DE 100 (USA) | 726 | 468 | 379 | 324 | 220 | — |
| | Insecolo (USA) (Baited Melocide) | 700 | 441 | — | — | — | — |
| | Melocide Super Fine (USA) | 600 | 436 | 324 | 266 | — | — |
| | DE Mexico 2 | 425 | 375 | 292 | — | — | — |
| | Perma Guard (USA) | 405 | — | — | — | — | — |
| | DE Mexico 1 | 375 | 299 | 265 | 213 | — | — |
| | DE San Diego (USA) | 370 | 327 | 285 | 243 | — | — |
| | DE Japan 1 | 360 | 300 | — | — | — | — |
| | Dryacide (Australia) | 285 | — | — | — | — | — |
| | Sipernat 50S (Canada) | 136 | — | — | — | — | — |

*Tapped density in DIN ISO 787/11 as the ratio of mass to volume of a substance which has been compacted in accordance with set conditions, expressed as g/l.
[1]Tapped densities are measured by Z. Korunic. The values serve only for comparison of differences of density of diatomaceous earths.

TABLE 5

THE EFFICACY OF SYNERGIZED CELITE 209 AND COMMERCIAL DE FORMULATIONS AGAINST FOUR STORED PRODUCT INSECTS AT 30° C., 14.6% M.C. ON WHEAT. THE CONCENTRATIONS FOR EACH INSECTS ARE: 300 PPM, RUSTY GRAIN BEETLE; 600 PPM LESSER GRAIN BORER AND RICE WEEVIL; 1000 PPM, RED FLOUR BEETLE

| | Mortality (%) | | | |
|---|---|---|---|---|
| Formulation | Rusty Grain Beetle | Lesser Grain Borer | Rice Weevil | Red Flour Beetle |
| Synergized Celite 209 | 93 | 79 | 94 | 96 |
| Celite 209 | 38 | 18 | 80 | 77 |
| Insecolo (Hedley) | 31 | 24 | 86 | 54 |
| Insecolo (USA) | 2 | 8 | 11 | 2 |
| Insecto | 29 | 12 | 81 | 38 |
| Dryacide | 26 | 19 | 96 | 80 |
| Perma Guard | — | 7 | 44 | — |
| DE Macedonia | 9 | 2 | 85 | 23 |
| DE Mexico | — | 0 | 20 | — |
| DE Japan 3 | — | 5 | 44 | — |
| Untreated | 1 | 7 | 6 | 0 |

TABLE 6

THE EFFICACY OF DIFFERENT CONCENTRATIONS OF
SYNERGIZED CELITE 209 AND INSECTO AGAINST
STORED-PRODUCT INSECTS AT 30° C., 15.6%
MC ON WHEAT

| | Rusty Grain Beetle | | | Rice Weevil | | | Red Flour Beetle | | | |
|---|---|---|---|---|---|---|---|---|---|---|
| | Concentration | Mortality (%) | | Concentration | Mortality (%) | | Concentration | Mortality (%) | | |
| Treatment | (ppm) | 7 days | 14 days | (ppm) | 7 days | 14 days | (ppm) | 7 days | 14 days | 21 days |
| Synergized | 50 | 45 | 88 | 100 | 18 | 21 | 300 | 1 | 0 | 0 |
| Celite 209 | 100 | 95 | 100 | 200 | 35 | 79 | 400 | 2 | 1 | 13 |
| | 150 | 96 | 100 | 300 | 71 | 92 | 500 | 6 | 13 | 42 |
| | 200 | 100 | 100 | 400 | 88 | 100 | 600 | 15 | 31 | 72 |
| Insecto | 50 | 21 | 71 | 100 | 9 | 27 | 300 | 0 | 1 | 1 |
| | 100 | 56 | 76 | 200 | 19 | 72 | 400 | 0 | 2 | 4 |
| | 150 | 59 | 83 | 300 | 33 | 83 | 500 | 2 | 2 | 14 |
| | 200 | 94 | 97 | 400 | 60 | 93 | 600 | 5 | 6 | 47 |
| Untreated | 0 | 6 | 14 | 0 | 1 | 1 | 0 | 0 | 0 | 0 |

Temperature: 30° C.; m.c. of wheat: 15.6%.

TABLE 7

COMPARISON TESTS BETWEEN SYNERGIZED CELITE 209
AND OTHER FORMULATIONS OF DIATOMACEOUS EARTH
FROM AROUND THE WORLD AGAINST THE RICE WEEVIL
ON WHEAT

| | | Mortality (%) after 5 days | | | | Mortality (%) after 10 days | | | |
|---|---|---|---|---|---|---|---|---|---|
| | | 20° C. | | 30° C. | | 20° C. | | 30° C. | |
| Formulation | Concentration (ppm) | 12% m.c. | 14% m.c. | 12% m.c. | 14% m.c. | 12% m.c. | 14% m.c. | 12% m.c. | 14% m.c. |
| Synergized Celite 209 | 400 | 97 | 60 | 97 | 68 | 99 | 77 | 99 | 86 |
| Insecto | 400 | 74 | 29 | 96 | 33 | 95 | 58 | 99 | 65 |
| Dryacide | 400 | 78 | 15 | 96 | 32 | 97 | 52 | 100 | 67 |
| Perma Guard | 400 | 23 | 7 | 56 | 2 | 72 | 14 | 85 | 10 |
| DE Japan 3 | 400 | 43 | 20 | 47 | 4 | 59 | 4 | 78 | 28 |
| Untreated | 0 | 1 | 0 | 15 | 2 | 2 | 15 | 0 | 1 |

TABLE 8

COMPARISON TESTS BETWEEN SYNERGIZED CELITE 209
AND OTHER FORMULATIONS OF DIATOMACEOUS EARTH
FROM AROUND THE WORLD AGAINST THE RED FLOUR
BEETLE AT 600 PPM

| | | Mortality (%) after 5 days | | | | Mortality (%) after 10 days | | | |
|---|---|---|---|---|---|---|---|---|---|
| | | 20° C. | | 30° C. | | 20° C. | | 30° C. | |
| Formulation | Concentration (ppm) | 12% m.c. | 14% m.c. | 12% m.c. | 14% m.c. | 12% m.c. | 14% m.c. | 12% m.c. | 14% m.c. |
| Synergized Celite 209 | 600 | 91 | 79 | 78 | 50 | 99 | 98 | 91 | 86 |
| Insecto | 600 | 63 | 19 | 28 | 3 | 96 | 59 | 92 | 57 |
| Dryacide | 600 | 68 | 36 | 31 | 6 | 89 | 68 | 69 | 52 |
| Perma Guard | 600 | 21 | 9 | 6 | 1 | 59 | 26 | 29 | 14 |
| DE Japan 3 | 600 | 55 | 12 | 29 | 1 | 59 | 34 | 72 | 29 |
| Untreated | 0 | 0 | 1 | 0 | 0 | 0 | 1 | 0 | 1 |

TABLE 9

THE SYNERGISM BETWEEN CELITE 209 AND PRECIPITATED SILICA SIPERNAT 50S AGAINST FOUR STORED-PRODUCT INSECTS

|  |  | Mortality (%) | | | Mortality (%) |  | Mortality (%) |
| --- | --- | --- | --- | --- | --- | --- | --- |
| Formulation | Concentration (ppm) | RGB 1 day | RW 5 days | Concentration (ppm) | LGB 6 days | Concentration (ppm) | RFB 7 days |
| Celite 209 | 270 | 28 | 25 | 540 | 18 | 900 | 76 |
| Sipernat 50S | 30 | 27 | 1 | 60 | 8 | 100 | 1 |
| Celite 209 + Sipernat 50S | 300 | 93 | 48 | 600 | 79 | 1000 | 96 |
| Untreated |  | 0 | 2 | 1 | 0 | 0 | 0 | 0 |

RGB - the rusty grain beetle; RW - the rice weevil; LGB - the lesser grain borer; RFB - the red flour beetle ' Temperature: 30° C.; RH: 70%; Grain: wheat.

TABLE 10

INSECTS EXTRACTED FROM WHEAT USING BERLESE FUNNELS. TWENTY GRAIN SAMPLES WERE TAKEN FROM EACH BIN ON AUGUST 30, 1994 AND OCTOBER 26 1994. THERE WERE APPROXIMATELY 40 TONNES OF GRAIN IN EACH BIN, WHICH HAD BEEN INFESTED WITH RUSTY GRAIN BEETLES AND RED FLOUR BEETLES ON 4 AUGUST 1994.

| Sampling Date | Concentration of Synergized Celite 209 | Rusty Grain Beetle | Red Flour Beetle | Beetle Larvae | Mites |
| --- | --- | --- | --- | --- | --- |
| Aug. 30 | 0 | $0.5 \pm 0.2$ a | $3.3 \pm 0.9$ a | $7.8 \pm 1.6$ a | $59 \pm 23$ a |
|  | 50 | $0.3 \pm 0.2$ a | $2.9 \pm 1.0$ a | $2.4 \pm 0.6$ b | $1 \pm 1$ b |
|  | 300 | $0.0 \pm 0.0$ a | $0.3 \pm 0.1$ b | $0.1 \pm 0.1$ c | $0 \pm 0$ c |
| Oct. 26 | 0 | $0.2 \pm 0.1$ a | $1.6 \pm 0.5$ a | $0.3 \pm 0.1$ a | $29 \pm 8$ a |
|  | 50 | $0.3 \pm 0.1$ a | $2.5 \pm 1.2$ a | $0.2 \pm 0.1$ a | $0.4 \pm 0.2$ b |
|  | 300 | $0.0 \pm 0.0$ a | $0.2 \pm 0.1$ b | $0.1 \pm 0.1$ a | $0.0 \pm 0.0$ b |

Average Number (/kg ± SEM)[1]

[1] For a given column and a given date, concentrations followed by different letters are significantly different (Kruskal-Wallis ANOVA, SNK Test)

TABLE 11

THE AVERAGE NUMBER OF RUSTY GRAIN BEETLES CAUGHT PER PROBE PIT FALL TRAP IN TWO WEEK PERIODS IN FIELD TRIALS. THERE WERE 20 TRAPS PER BIN, 10 AT THE SURFACE AND 10 AT 1 METRE BELOW THE SURFACE.

| Concentration of Synergized Celite 209 (ppm) | Rusty Grain Beetle/Trap/Two Weeks (mean ± SEM) Date Trapping Finished | | | | |
| --- | --- | --- | --- | --- | --- |
|  | Aug. 30 | Sept. 12 | Sept. 28 | Oct. 12 | Oct. 26 |
| 0 | $17 \pm 6$ a | $5 \pm 1$ a | $5 \pm 1$ a | $2 \pm 1$ a | $3 \pm 1$ a |
| 50 | $16 \pm 5$ a | $1 \pm 0.3$ b | $1 \pm 0.3$ b | $6 \pm 4$ a | $1 \pm 0.4$ b |
| 300 | $1 \pm 0.3$ b | $0 \pm 0$ c | $0 \pm 0$ c | $0 \pm 0$ c | $0 \pm 0$ c |

[1] For a given column, concentrations followed by different letters are significantly different (Kruskal-Wallis ANOVA, SNK Test).

TABLE 12

THE AVERAGE NUMBER OF RED FLOUR BEETLES CAUGHT PER PROBE PIT FALL TRAP IN TWO-WEEK PERIODS IN FIELD TRIALS. THERE WERE 20 TRAPS PER BIN, 10 AT THE SURFACE AND 10 AT 1 METRE BELOW THE SURFACE.

| Concentration of Synergized Celite 209 | Red Flour Beetle/Trap/Two Weeks Date Trapping Finished | | | | |
|---|---|---|---|---|---|
| (ppm) | Aug. 30 | Sept. 12 | Sept. 28 | Oct. 12 | Oct. 26 |
| 0 | 215 ± 60 a | 79 ± 19 a | 100 ± 15 a | 16 ± 3 a | 14 ± 3 a |
| 50 | 157 ± 36 a | 32 ± 10 b | 42 ± 10 b | 19 ± 6 a | 12 ± 5 a |
| 300 | 110 ± 38 b | 4 ± 1 c | 1 ± 0.3 c | 1 ± 0.3 c | 0.2 ± 0.1 c |

[1]For a given column, concentrations followed by different letters are significantly different (Kruskal-Wallis ANOVA, SNK Test).

TABLE 13

THE AVERAGE BULK DENSITIES (TEST WEIGHTS), MOISTURE CONTENTS AND GRADES (GRADED BY CANADIAN GRAIN COMMISSION) FROM FIELD TRIALS.

| Date Sampled | Concentration of Synergized Celite 209 (ppm) | Bulk Density[1] (kg/hl) | Moisture[1] Content (%) | Grade |
|---|---|---|---|---|
| Aug. 30 | 0 | 75.6 ± 0.2 a | 13.6 ± 0.1 a | 2 |
|  | 50 | 73.5 ± 0.2 b | 13.0 ± 0.02 b | 2 |
|  | 300 | 70.8 ± 0.2 c | 13.0 ± 0.1 b | 2 |
| Oct. 27 | 0 | 75.3 ± 0.2 a | 14.0 ± 0.1 a | — |
|  | 50 | 73.2 ± 0.2 b | 13.5 ± 0.1 b | — |
|  | 300 | 70.7 ± 0.2 c | 13.6 ± 0.1 b | — |

[1]For a given column, concentrations are significantly different if followed by a different letter (Kruskal-Wallis ANOVA, Dunn's Test), 20 samples/bin except for grade which had 1 sample/bin

TABLE 14

THE EFFICACY OF THE MIXTURE OF DIFFERENT FORMULATIONS OF DIATOMACEOUS EARTH AND PRECIPITATED SILICA SIPERNAT 50S (60% DE + 40% SIPERNANT 50S) AGAINST THE RED FLOUR BEETLE (RFB) AND THE LESSER GRAIN BORER (LGB), AT 30° C., 13.6% M.C. ON WHEAT AT CONCENTRATION OF 800 PPM

| | Mortality (%) | | | |
|---|---|---|---|---|
| | RFB | | LGB | |
| Combinations | 1 day | 2 days | 1 day | 2 days |
| Untreated | 0 | 0 | 0 | 0 |
| DE Europe + Silica | 88 | 93 | 78 | 89 |
| Melocide Super Fine + Silica | 94 | 99 | 90 | 96 |
| Insecolo (Hedley) + Silica | 98 | 99 | 76 | 96 |
| Celite 209 + Silica | 92 | 99 | 78 | 93 |
| Snow Floss + Silica | 92 | 98 | 68 | 93 |
| Melocide DE 100 + Silica | 83 | 86 | 81 | 94 |

TABLE 15

THE EFFICACY OF SYNERGIZED DIATOMACEOUS EARTH AGAINST THE RICE WEEVIL, (RW) THE LESSER GRAIN BORER (LGB) AND THE RED FLOUR BEETLE (RFB) AT 30° C., 13.6% M.C.

| | | Mortality (%) 7 days | | |
|---|---|---|---|---|
| Formulation | Concentration (ppm) | RW | LGB | RFB |
| Melocide DE 100 + Sipernat 50S (mixture 90:10) | 540 + 60 (mixture 600) | 27 | 23 | 10 |
| Melocide DE 100 | 600 | 8 | 0 | 0 |
| DE Macedonia (Europe) + Sipernat 50S (mixture 80:20) | 480 + 120 (mixture 600) | 97 | 64 | 69 |
| DE Macedonia (Europe) | 600 | 64 | 35 | 6 |
| Celite 209 + Sipernat 50S (mixture 90:10) | 540 + 60 (mixture 600) | 99 | 53 | 83 |
| Celite 209 | 600 | 68 | 39 | 37 |
| Untreated | 0 | 1 | 0 | 0 |

TABLE 16

THE EFFICACY OF SYNERGIZED DIATOMACEOUS EARTH AGAINST THE RED FLOUR BEETLE (RFB), THE LESSER GRAIN BORER (LGB), THE RICE WEEVIL (RW) AND THE RUSTY GRAIN BEETLE (RGB) AT 30° C., 14.0% MC ON WHEAT

| | | Mortality (%) | | | |
|---|---|---|---|---|---|
| | Concentration | 3 days | 6 days | | |
| Formulation | (ppm) | RGB | RW | RFB | LGB |
| Control | 0 | 3 | 3 | 1 | 2 |
| Celite 209 + Sipernat 50S (mixture 90:10) | 540 60 (mixture 600) | 100 | 71 | 6 | 41 |
| Celite 209 | 600 | 100 | 35 | 1 | 23 |
| DE Macedonia + Sipernat 50S (mixture 80:20) | 480 120 (mixture 600) | 100 | 82 | 6 | 26 |
| DE Macedonia | 600 | 100 | 56 | 0 | 8 |
| Dryacide | 600 | 100 | 52 | 2 | 14 |

TABLE 17

THE EFFICACY OF SYNERGIZED DIATOMACEOUS EARTH AGAINST THE RUSTY GRAIN BEETLE (RGB), THE RICE WEEVIL (RW), THE LESSER GRAIN BORER (LGB), AND THE RED FLOUR BEETLE (RFB) AT 30° C., 14.1% MC ON WHEAT

| | Mortality (%) | | | |
|---|---|---|---|---|
| | RGB | RW | LGB | RFB |
| | 300 ppm | 300 ppm | 1000 ppm | 1000 ppm |
| Formulation | 1 day | 5 days | 2 days | 7 days |
| Celite 209 + Sipernat 50S | 94 | 68 | 92 | 96 |
| Celite 209 | 38 | 28 | 49 | 77 |
| Snow Floss + Sipernat 50S | 90 | 77 | 54 | 94 |
| Snow Floss | 41 | 42 | 29 | 82 |
| DE Macedonia + Sipernat 50S | 73 | 28 | 67 | 81 |
| DE Macedonia (Europe) | 9 | 11 | 64 | 23 |
| Melocide DE 100 + Sipernat 50S | 68 | 20 | 54 | 11 |
| Melocide DE 100 | 4 | 4 | 0 | 2 |
| Insecto | 30 | 24 | 74 | 38 |
| Insecolo (HPV) | 30 | 37 | 68 | 54 |
| Dryacide | 23 | 48 | 67 | 80 |

TABLE 18

THE ENHANCEMENT OF EFFICACY OF DIATOMACEOUS EARTHS MIXED WITH SYNERGIST SIPERNAT 50S IN DIFFERENT RATIOS AGAINST THE RICE WEEVIL AT 30° C., 13.9% M.C. ON WHEAT

| | | Mortality % Sipernat 50S - Percentage (w/w) in Mixture | | | |
|---|---|---|---|---|---|
| Formulation | Duration | | | | |
| (300 ppm) | (days) | 0 | 10 | 20 | 30 |
| Marine Diatomaceous Earths | | | | | |
| DEMacedonia (Europe) | 2 | 31 | 48 | 77 | 76 |
| | 7 | 71 | 86 | 94 | 94 |
| DE Japan 2 | 2 | 20 | — | 58 | — |
| | 7 | 56 | — | 82 | — |
| Celite 209 (USA) | 2 | 28 | 64 | — | — |
| | 7 | 65 | 88 | — | — |
| Snow Floss (USA) | 2 | 31 | — | — | — |
| | 7 | 67 | — | — | — |
| DE Japan 3 | 2 | 10 | 44 | — | — |
| | 7 | 38 | 68 | — | — |
| Fresh Water Diatomaceous Earths | | | | | |
| Melocide DE 100 (USA) | 2 | 6 | 14 | 46 | 53 |
| | 7 | 22 | 42 | 74 | 78 |
| Melocide Super Fine (USA) | 2 | 7 | 26 | 61 | 68 |
| | 7 | 28 | 58 | 85 | 93 |
| DE Mexico 2 | 2 | 13 | 44 | 46 | — |
| | 7 | 39 | 66 | 77 | — |
| DE Mexico 1 | 2 | 15 | 35 | 56 | — |
| | 7 | 34 | 66 | 78 | — |
| DE San Diego (USA) | 2 | 18 | 43 | 73 | — |
| | 7 | 35 | 62 | 88 | — |
| DE Japan 1 | 2 | 25 | 52 | — | — |
| | 7 | 47 | 78 | — | — |
| Dryacide Australia | 2 | 46 | | | |
| | 7 | 75 | | | |
| Sipernat 50S - 30 ppm (10% in mixture) | 2 | 6 | | | |
| | 7 | 7 | | | |
| Sipernat 50S - 60 ppm (20% in mixture) | 2 | 8 | | | |
| | 7 | 20 | | | |
| Sipernat 50S - 90 ppm (30% in mixture) | 2 | 27 | | | |
| | 7 | 38 | | | |

TABLE 19

THE ENHANCEMENT OF EFFICACY OF DIATOMACEOUS EARTHS MIXED WITH SYNERGIST SIPERNAT 50S IN DIFFERENT RATIOS AGAINST THE RED FLOUR BEETLE AT 30° C., 13.9% M.C. ON WHEAT

| | | Mortality (%) Sipernat 50S - Percentage (w/w) in Mixture | | | |
|---|---|---|---|---|---|
| Formulation | Duration | | | | |
| (ppm) | (days) | 0 | 10 | 20 | 30 |
| Marine Diatomaceous Earths | | | | | |
| DE Macedonia (Europe) | 14 | 13 | 26 | 63 | 33 |
| | 21 | 46 | 46 | 86 | 46 |
| | 28 | 79 | 87 | 97 | 74 |
| DE Japan 2 | 14 | 0 | — | 0 | — |
| | 21 | 3 | — | 0 | — |
| | 28 | 13 | — | 100 | — |
| Celite 209 (USA) | 14 | 26 | 33 | — | — |
| | 21 | 81 | 84 | — | — |
| | 28 | 93 | 93 | — | — |
| Snow Floss (USA) | 14 | 20 | — | — | — |
| | 21 | 72 | — | — | — |
| | 28 | 97 | — | — | — |
| DE Japan 3 | 14 | 0 | 7 | — | — |
| | 21 | 0 | 14 | — | — |
| | 28 | 10 | 24 | — | — |
| Fresh Water Diatomaceous Earths | | | | | |
| Melocide DE 100 (USA) | 14 | 0 | 0 | 0 | 7 |
| | 21 | 3 | 0 | 0 | 7 |
| | 28 | 3 | 0 | 7 | 10 |
| Melocide Super Fine (USA) | 14 | 0 | 0 | 0 | 10 |
| | 21 | 0 | 0 | 3 | 10 |
| | 28 | 0 | 0 | 3 | 10 |
| DE Mexico 2 | 14 | 0 | 0 | 0 | — |
| | 21 | 0 | 0 | 0 | — |
| | 28 | 3 | 10 | 10 | — |
| DE Mexico 1 | 14 | 0 | 0 | 4 | — |
| | 21 | 0 | 0 | 4 | — |
| | 28 | 3 | 10 | 10 | — |
| DE San Diego (USA) | 14 | 0 | 0 | 7 | — |
| | 21 | 3 | 0 | 13 | — |
| | 28 | 3 | 0 | 22 | — |
| DE Japan 1 | 14 | 0 | 0 | — | — |
| | 21 | 3 | 3 | — | — |
| | 28 | 13 | 13 | — | — |
| Dryacide Australia | 14 | 13 | | | |
| | 21 | 55 | | | |
| | 28 | 92 | | | |
| Sipernat 50S - 30 ppm (10% in mixture) | 14 | 0 | | | |
| | 21 | 0 | | | |
| | 28 | 0 | | | |
| Sipernat 50S - 60 ppm (20% in mixture) | 14 | 0 | | | |
| | 21 | 3 | | | |
| | 28 | 3 | | | |

TABLE 19-continued

THE ENHANCEMENT OF EFFICACY OF DIATOMACEOUS EARTHS MIXED WITH SYNERGIST SIPERNAT 50S IN DIFFERENT RATIOS AGAINST THE RED FLOUR BEETLE AT 30° C., 13.9% M.C. ON WHEAT

| Formulation | Duration | Mortality (%) Sipernat 50S - Percentage (w/w) in Mixture | | | |
|---|---|---|---|---|---|
| (ppm) | (days) | 0 | 10 | 20 | 30 |
| Sipernat 50S - 90 ppm | 14 | 0 | | | |
| (30% in mixture) | 21 | 0 | | | |
| | 28 | 0 | | | |

TABLE 20

PERCENT REDUCTION OF INSECTS CAUGHT OVER A 6 WEEK PERIOD. WHEAT WAS TREATED WITH PROTECT-IT AS A DUST OR AS A SPRAY (100 S) AND THE NUMBER OF INSECT CAUGHT IN PROBE-PIT FALL TRAPS WERE COMPARED WITH THE NUMBER OF INSECTS CAUGHT IN UNTRETAED BINS AT EACH SITE.

| | Rusty Grain Beetle | | | Red Flour Beetle | | |
|---|---|---|---|---|---|---|
| Dose (ppm) | Winnipeg | University of Manitoba | Morden | Winnipeg | University of Manitoba | Morden |
| 75 | 99.8 | 99.2 | 98.5 | 25.3 | 16.7 | + |
| 100 | 99.9 | 99.7 | 100 | 83.0 | 73.8 | 6.8 |
| 100S | — | 99.9 | 87.4 | — | 47.6 | 56.8 |

+ population higher than control.

TABLE 21

THE AVERAGE NUMBER OF ALIVE ADULTS OF THE RUSTY GRAIN BEETLE (RGB) AND THE RED FLOUR BEETLE (RFB) PER KG OF GRAIN IN GRANARIES TREATED WITH PROTECT-IT WITH DIFFERENT CONCENTRATIONS AND METHODS OF APPLICATION
Field tests in 1995

| Concentration (ppm) and method of application | Average number of alive adults/kg of wheat | | | | | |
|---|---|---|---|---|---|---|
| | WRC after 46 days | | U of M after 55 days | | Morden after 50 days | |
| | RGB | RFB | RGB | RFB | RGB | RFB |
| 0 ppm | 0.4 a (0.60) | 0.6 a (0.74) | 2.3 a (1.89) | 0.4 a (0.40) | 0.8 a (0.75) | 1.9 a (2.57) |
| 75 ppm dusting | 0.0 b (0.00) | 0.2 a,b (0.35) | 0.0 b | 0.06 a,b (0.12) | 0.0 b (0.00) | 0.4 a,b (0.67) |
| 100 ppm dusting | 0.0 b (0.00) | 0.1 b (0.38) | 0.0 b (0.0) | 0.0.0 b | 0.0 b (0.00) | 0.3 a,b (0.55) |
| 100 ppm spraying | — | — | 0.0 b | 0.0.2 a,b (0.47) | 0.1 b (0.25) | 0.1 b (0.25) |

ANOVA, Tukey (HSD). Rejection level - 0.050. For a given column, means followed by the same letter are not significantly different.
() = standard deviation
WRC = Winnipeg Research Centre Experimental Field Station, Glenlea
U of M = University of Manitoba Experimental Station, Glenlea
Morden = Experimental Station Morden
WRC - 20 profile probe samples (about 1.2 kg each) from each granary
U of M - 10 profile probe samples (about 1.9 kg each) from each granary
Morden - 10 profile probe sample (about 2 kg each) from each granary
Profile samples taken from the pitfall probe trap points and between them.

TABLE 22

THE EFFICACY OF PROTECT-IT AGAINST THE RUSTY GRAIN BEETLE AND THE RED FLOUR BEETLE ON HARD RED SPRING WHEAT IN SMALL-SCALE TESTS UNDER FIELD CONDITIONS
Site 1. Winnipeg Research Centre Experimental Field Station, Glenlea

| Concentration (ppm) | Number of alive insects/ jar after 56 days | | | | Test weight[1] Mean (Std. dev.) (kg/hL) | Dockage Mean (Std. dev.) (%) | Moisture* content Mean (Std. de.) (%) | Grain temperature in jars (°C.) | |
|---|---|---|---|---|---|---|---|---|---|
| | RGB | | RFB | | | | | | |
| | Mean (Std. dev.) | Population reduction (%) | Mean (Std. dev.) | Population reduction (%) | | | | At start | At the end |
| 0 | 87.7 a (30.66) | — | 53.3 a (21.22) | — | 77.7 a (0.28) | 1.0 a (0.18) | 13.6 a (0.51) | 25.0 | 2.4 |
| 75 | 0.3 b (0.57) | 99.6 | 13.0 a (13.75) | 75.6 | 74.9 b (0.97) | 1.1 a (0.02) | 13.2 a (0.11) | 23.0 | 1.8 |
| 100 | 0.7 b (1.15) | 99.2 | 23.0 a (18.03) | 62.5 | 74.6 b (0.89) | 1.2 a (0.14) | 13.3 a (0.11) | 18.6 | 2.0 |

ANOVA, Tukey (HSD). Rejection level - 0.050. For a given column, means followed by the same letter are not significantly different.
[1]measured by Winnipeg Research Centre
*moisture content (%) at the beginning of the test: 0 ppm - 13.2 to 14.1; 75 ppm - 13.4 to 14.1; 100 ppm - 13.0 to 13.1.

TABLE 23

THE EFFICACY OF PROTECT-IT AGAINST THE RUSTY GRAIN
BEETLE (RGB) AND THE RED FLOUR BEETLE (RFB) ON
HARD RED SPRING WHEAT IN SMALL-SCALE TESTS UNDER
FIELD CONDITIONS
Site 2. University of Manitoba Experimentl Station, Glenlea

| Concentration (ppm) | Number of alive insects/jar after 56 days | | | | Test weight[1] (kg/hL) Mean (Std. dev.) | Dockage (%) Mean (Std. dev.) | Moisture* content (%) Mean (Std. de.) | Grain temperature in jars (°C.) | |
|---|---|---|---|---|---|---|---|---|---|
| | RGB | | RFB | | | | | | |
| | Mean (Std. dev.) | Population reduction (%) | Mean (Std. dev.) | Population reduction (%) | | | | At start | At the end |
| 0 | 70.3 a (25.01) | — | 56.7 a (32.72) | — | 77.0 a (0.28) | 1.5 a (0.22) | 14.3 a (0.73) | 25.6 | 2.3 |
| 75 | 0.7 b (0.57) | 99.0 | 56.3 a (24.50) | 0.7 | 74.3 c (0.18) | 0.9 b (0.06) | 14.0 b (0.05) | 24.3 | 1.7 |
| 100 | 0.0 b (0.00) | 100.0 | 6.3 b (0.57) | 88.9 | 73.2 c (0.30) | 1.1 a,b (0.31) | 13.3 c (0.05) | 23.6 | 1.4 |
| 100 spray. | 4.0 b (1.00) | 93.4 | 31.0 a (10.39) | 45.3 | 74.6 b (0.23) | 1.4 a,b (0.11) | 13.9 b (0.05) | 23.9 | 2.0 |

ANOVA, Tukey (HSD). Rejection level - 0.050. For a given column, means followed by the same letter are not significantly different.
[1]measured by Winnipeg Research Centre
*moisture content (%) at the beginning of the test: 0 ppm - 14.5 to 14.7; 75 ppm - 14.0 to 14.5; 100 ppm - 13.5 to 14.7; 100 ppm spraying - 14.0 to 14.5.

TABLE 24

THE EFFICACY OF PROTECT-IT AGAINST THE RUSTY GRAIN
BEETLE (RGB) AND THE RED FLOUR BEETLE (RFB) ON
HARD RED SPRING WHEAT IN SMALL-SCALE TESTS UNDER
FIELD CONDITIONS
Site 3. Experimental Station, Morden

| Concentration (ppm) | Number of alive insects/jar after 56 days | | | | Test weight[1] (kg/hL) Mean (Std. dev.) | Dockage (%) Mean (Std. dev.) | Moisture* content (%) Mean (Std. dev.) | Grain temperature in jars (°C.) | |
|---|---|---|---|---|---|---|---|---|---|
| | RGB | | RFB | | | | | | |
| | Mean (Std. dev.) | Population reduction (%) | Mean (Std. dev.) | Population reduction (%) | | | | At start | At the end |
| 0 | 54.0 a (14.42) | — | 112.3 a (40.87) | — | 70.6 | 1.9 a (0.11) | 12.6 a (0.05) | 27.1 | 5.1 |
| 75 | 0.7 b (1.15) | 98.7 | 59.7 a (37.87) | 46.8 | 73.4 | 1.0 b (0.15) | 13.6 b (0.26) | 20.5 | 3.3 |
| 100 | 0.0 b (0.00) | 100.0 | 59.3 a (5.77) | 47.2 | 73.2 | 0.6 c (0.05) | 13.4 b (0.10) | 22.0 | 3.2 |
| 100 spray. | 4.0 b (3.46) | 92.6 | 83.0 a (7.93) | 26.1 | 74.0 | 0.6 c (0.20) | 13.4 b (0.10) | 20.3 | 3.6 |

ANOVA, Tukey (HSD). Rejection level - 0.050. For a given column, means followed by the same letter are not significantly different.
[1]measured by Winnipeg Research Centre
*moisture content (%) at the beginning of the test: 0 ppm - 12.6; 75 ppm - 13.4 to 14.8; 100 ppm - 13.7 to 14.7; 100 ppm spraying - 13.2 to 13.7.
In each granary at the date of introducing insects, 3 jars (height 25 cm, diametre 15 cm) were filled with HRS wheat (about 3 kg) after the grain was treated. After that 200 RGB and 200 RFB were introduced in each jar. Jars were closed with lids with the oppenings covered with wire and inserted in the surface layers in each granary.

TABLE 25

THE REDUCTION OF TEST WEIGHT (BULK DENSITY) BY
PROTECT-IT ON HARD RED SPRING WHEAT AS COMPARED
TO UNTREATED WHEAT, MEASURED AND GRADED BY
CANADIAN GRAIN COMMISSION (CGC)
FIELD TESTS WITH PROTECT-IT IN 1995

Site 1. Winnipeg Research Centre Experimental Field Station, Glenlea

| Concen- | Test weight (kg/hL) | | | Difference (kg/hL) | | Grading | | |
|---|---|---|---|---|---|---|---|---|
| tration (ppm) | Before tretment* | 0 day after treatment** | 74 days after treatment | 0 day after tretament | 74 days after treatment | Before treatment | 0 day after treatment | 74 days after treatment |
| 0 | 79.4 a | 78.9 | 78.0 b | 0.5 | 1.4 | 2 | 2 | 2 |
| 75 | 79 a | 76.7 | 75.3 b | 2.3 | 3.7 | 2 | 1;2 | 2 |
| 100 | 78.6 a | 76.5 | 74.8 b | 2.1 | 3.8 | 1;2 | 1;2 | 1;2 |

Site 2. University of Manitoba, Experimental Station Glenlea

| Concen- | Test weight (kg/hL) | | | Difference (kg/hL) | | Grading | | |
|---|---|---|---|---|---|---|---|---|
| tration (ppm) | Before tretment* | 0 day after treatmnet** | 84 days after treatment | 0 day after tretament | 84 days after treatment | Before treatment | 0 day after tretament | 84 days after treatment |
| 0 | 79.1 a | 78.7 | 78.1 b | 0.4 | 1.0 | 1 | 1 | 1 |
| 75 | 79.4 a | 77.4 | 75.7 b | 2.0 | 3.7 | 1 | 1 | 1 |
| 100 | 79.2 a | 76.3 | 75.0 b | 2.9 | 4.2 | 1;2 | 1 | 1 |
| 100 spray | 78.6 a | 76.0 | 76.0 b | 2.6 | 2.6 | 1 | 1 | 1 |

Site 3. Experimental Station Morden

| Concen- | Test weight (kg/hL) | | | Difference (kg/hL) | | Grading | | |
|---|---|---|---|---|---|---|---|---|
| tration (ppm) | Before tretment* | 0 day after treatmnet** | 76 days after treatment | 0 day after tretament | 76 days after treatment | Before treatment | 0 day after tretament | 76 days after treatment |
| 0 | 72.6 a | 72.6 | 72.6 b | 0.0 | 0.0 | 2;3 | 2;3 | 2 |
| 75 | 77.5 a | 76.1 | 75.0 b | 1.4 | 2.5 | 2;3 | 2;3 | 2;3 |
| 100 | 78.1 a | 76.1 | 75.4 b | 2.0 | 2.7 | 2;3 | 2 | 2 |
| 100 spray | 78.1 a | 76.1 | 75.7 b | 2.0 | 2.4 | 2;3 | 2 | 3 |

ANOVA, Tukey (HSD). Rejection level - 0.050. Means in rows folowed by the same letter are not significantly different.
*samples from a truck before unloading
**2 samples graded from a bin after treatment and loading The claimed invention is:

1. An insecticidal dust composition consisting of a mixture of about 95% to 65% by weight diatomaceous earth (DE) and about 5% to 35% by weight silica selected from the group consisting of precipitated silica and aerogel silica, wherein the DE and silica are present in a combined synergistic insecticidally effective amount.

2. A composition according to claim 1 wherein the DE has a median particle size from about 4.5 microns to about 12 microns, with at least more than 65% particles below 16 microns.

3. A composition according to claim 2 wherein the DE is selected from the groups of marine and fresh water DE.

4. A composition according to claim 1 wherein the silica is of a particle size in the range of about 4 microns to about 10 microns.

5. A composition according to claim 4 wherein the silica is precipitated amorphous silica.

6. A composition according to claim 3 wherein the silica is of a particle size of 8 microns and the silica is precipitated amorphous silica.

7. A composition according to claim 6 wherein the DE is about 90% by weight marine DE and the silica is about 10% by weight precipitated amorphous silica.

8. A composition of claim 1, wherein the silica is aerogel silica.

9. A composition of claim 1, wherein the silica is precipitated amorphous silica.

10. A composition according to claim 1, wherein the DE is about 90% by weight marine DE and the silica is about 10% by weight precipitated amorphous silica.

* * * * *